United States Patent [19]

Counsell et al.

[11] Patent Number: 5,795,561

[45] Date of Patent: *Aug. 18, 1998

[54] RADIOIODINATED PHOSPHOLIPID ETHER ANALOGUES

[75] Inventors: Raymond E. Counsell, Ann Arbor, Mich.; Karen L. Meyer, Norman, Okla.; Susan W. Schwendner, Ann Arbor, Mich.; Terushi Haradahira, Fukuoka, Japan

[73] Assignee: The Board of Regents of the University of Michigan, Ann Arbor, Mich.

[*] Notice: The term of this patent shall not extend beyond the expiration date of Pat. Nos. 4,965,391 and 5,347,030.

[21] Appl. No.: 304,259

[22] Filed: Sep. 12, 1994

Related U.S. Application Data

[60] Continuation of Ser. No. 833,303, Feb. 10, 1992, Pat. No. 5,347,030, which is a division of Ser. No. 602,157, Oct. 22, 1990, Pat. No. 5,087,721, which is a continuation-in-part of Ser. No. 573,586, Aug. 27, 1990, abandoned, which is a continuation of Ser. No. 112,865, Oct. 23, 1987, Pat. No. 4,965,391.

[51] Int. Cl.$^6$ .................. A61K 51/00; A61M 36/14
[52] U.S. Cl. ............ 424/1.77; 424/1.65; 424/1.85
[58] Field of Search .................... 558/169, 166; 424/1.77, 1.81, 1.85, 1.65

[56] References Cited

U.S. PATENT DOCUMENTS

| | | | |
|---|---|---|---|
| 3,716,631 | 2/1973 | Steggerda et al. | 424/1 |
| 4,473,544 | 9/1984 | Maehulla et al. | 424/1.1 |
| 4,571,332 | 2/1986 | Schroit et al. | 424/1.1 |
| 4,925,649 | 5/1990 | Counsell et al. | 424/1.1 |
| 4,965,391 | 10/1990 | Counsell et al. | 558/169 |
| 5,061,626 | 10/1991 | Baldo et al. | 435/174 |
| 5,087,721 | 2/1992 | Counsell et al. | 558/166 |
| 5,347,030 | 9/1994 | Counsell et al. | 558/169 |

OTHER PUBLICATIONS

Andreesen et al., *Cancer Research*, vol. 38, pp. 3894–3899, Nov., 1978.

March et al., *Advanced Organic Chemistry*, p. 1100, 1985.

*Primary Examiner*—John Kight
*Assistant Examiner*—Dameron Jones
*Attorney, Agent, or Firm*—Rohm & Monsanto

[57] ABSTRACT

Novel radioiodinated analogues of naturally-occurring phospholipid ethers are tumor-specific and have a triglycerol backbone structure which, in certain embodiments, is substituted at the 3-position with an alkyl phosphocholine and include a monoiodinated benzoyl side chain substituted at the 2-position in accordance with the general formula:

$$\begin{array}{c} CH_3(CH_2)_n-O-CH_2 \\ \phantom{CH_3(CH_2)_n-O-}\,\,\,\,\,\,\,\,\,\,\,\,\,\,\,\,\,\,\,\,\,\,\,\,\,\,\,\,\,\,\,\,\,\,\,| \\ \phantom{xxxxxxxxxx}O\phantom{xxxx}CH-X \\ \phantom{xxxxxxxxxx}\|\phantom{xxxxx}| \\ Y-CH_2-CH_2-O-P-O-CH_2 \\ \phantom{xxxxxxxxxxxxxxxxxxxxx}| \\ \phantom{xxxxxxxxxxxxxxxxxxxxx}OH \end{array}$$

where n=1–15

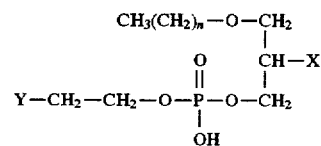

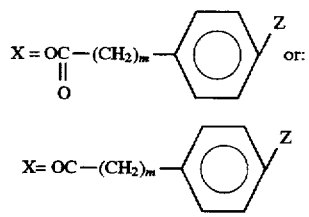

M=0–15; Z=$^{123}$I, $^{125}$I, and $^{131}$I; Y=NH$_2$, NR$_2$, and NR$_3$, and R=alkyl, aralkyl.

2 Claims, 11 Drawing Sheets

ET-121P-OMe IN TUMORED RAT

ET-121P-OMe IN TUMORED RAT

ET-121P-OMe IN CARRAGEENEN RAT

ET-121P-OMe IN CARRAGEENEN RAT

GALLIUM-67 CITRATE IN CARRAGEENEN RAT

GALLIUM-67 CITRATE IN CARRAGEENEN RAT

GALLIUM-67 RAT

GALLIUM-67 RAT

1-ALKYL-2-ACYL-SN-GLYCERO-
3-PHOSPHOCHOLINE

↓ PHOSPHOLIPASE $A_2$

ALKYL LYSOPHOSPHATIDYLCHOLINE

↓ 1-O-ALKYL CLEAVAGE ENZYME

SN-GLYCERO-3-PHOSPHOCHOLINE

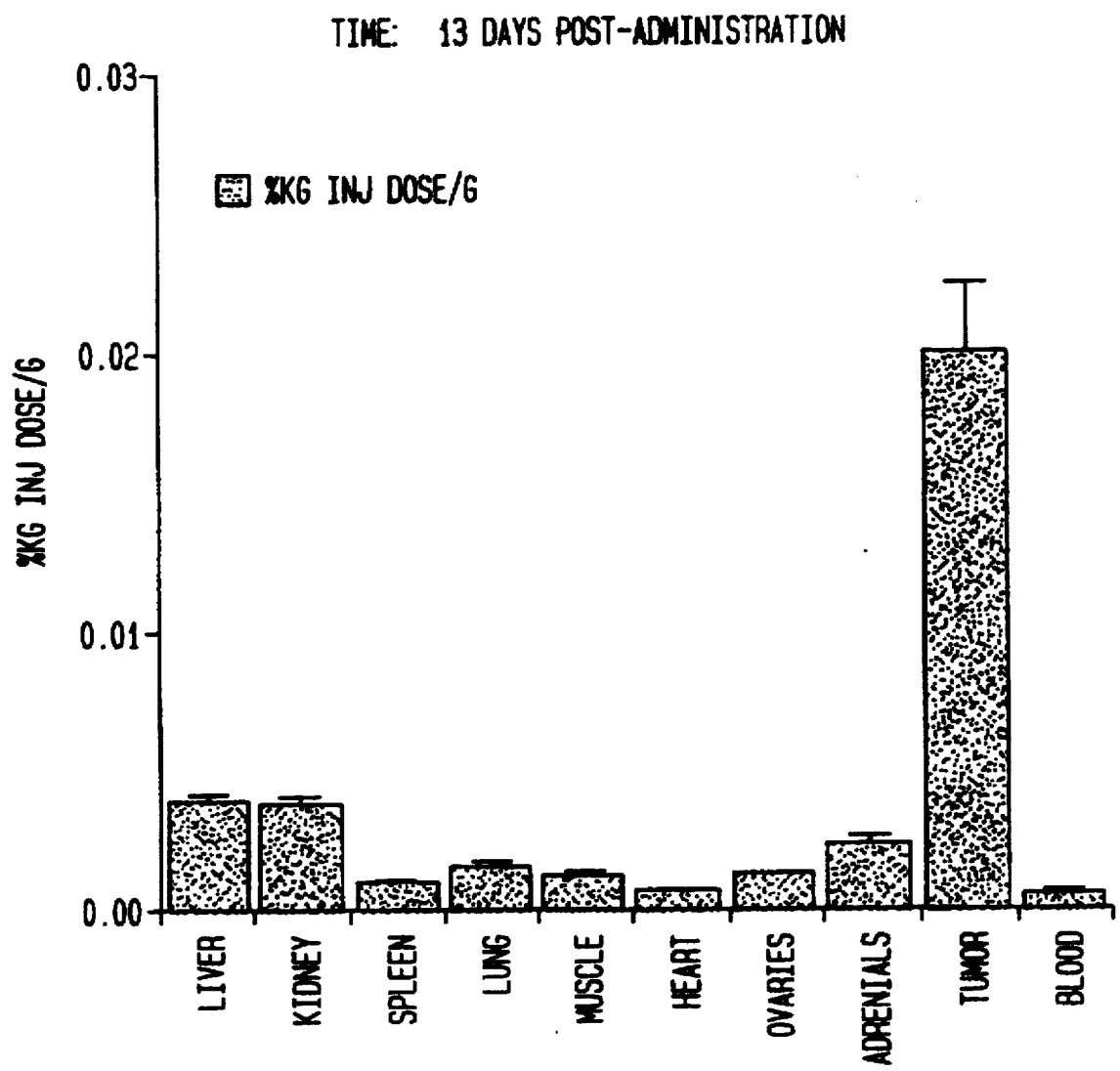

RADIOIODINATED PHOSPHOLIPID ETHER ANALOGUES

RELATIONSHIP TO OTHER APPLICATION

This application is a continuation of United States patent application Ser. No. 07/833,303 filed on Feb. 10, 1992, now U.S. Pat. No. 5,347,030, as a division of United States patent application Ser. No. 07/602,157 filed on Oct. 22, 1990, now U.S. Pat. No. 5,087,721, application Ser. No. 07/602,157 was a continuation-in-part of U.S. patent application Ser. No. 07/573,586 filed on Aug. 27, 1990, now abandoned, which was a continuation of Ser. No. 07/112,865 filed on Oct. 23, 1987, now U.S. Pat. No. 4,965,391, all applications being assigned to the assignee hereof.

GOVERMENT RIGHTS

This invention was sponsored by the Department of Health & Human Services under Grant Number CA 008349, and therefore the United States government may have certain rights in this invention.

BACKGROUND OF THE INVENTION

This invention relates to radioiodinated compounds which are useful as radiopharmaceuticals and biological probes, and more specifically, to radioiodinated phospholipid analogues of the naturally-occurring ether, alkyl lysophospholipid, and alkyl phosphocholine which are tumor-specific and can be used for gamma camera scintigraphy.

Currently, most scintigraphic procedures for tumor-imaging utilize organ-specific radiodiagnostics which rely upon alteration of the radioactivity distribution within normal tissue for external visualization of tumors. The variations may appear as either an area of increased, or decreased, radioactivity within the tissue. A problem which has been encountered with these known radiodiagnostics is that many biological conditions, such as abscesses or other inflammations, can cause a disturbance in the radioactivity distribution pattern.

There are presently not available radiopharmaceuticals which will specifically image neoplastic lesions by non-invasive nuclear medicine techniques. The current radiodiagnostic agent of choice for scintigraphy, gallium-67 citrate, will localize, or accumulate, in a tumor causing it to appear as an area of increased radioactivity when examined externally via a gamma camera. However, gallium-67 citrate is not tumor-specific (defined herein as localizing only in tumors) since it also accumulates in a variety of other inflammatory lesions. In addition, normal liver and spleen tissue typically exhibit high concentrations of radioactivity with the use of gallium-67 citrate. As a result, it is difficult to identify abnormal accumulations of radioactivity in or adjacent to these tissues. An additional disadvantage of gallium-67 citrate is that the distribution of this agent can be altered by a variety of steroidal and antineoplastic drugs. Thus, the usefulness of gallium-67 citrate is limited after chemotherapy has been initiated.

Other tumor-localizing agents such as selenomethionine [$^{75}$Se] and bleomycin labelled with $^{111}$In, $^{57}$Co, or $^{99}$Tc, have been investigated. However, these agents are not tumor-specific, nor have they exhibited any obvious advantages over gallium-67 citrate.

Monoclonal antibodies have been developed which are tumor-specific. However, monoclonal antibodies are specific only to the particular tumor tissue for which they have been produced and will not localize generally in neoplastic tissue. Moreover, the use of monoclonal antibodies can result in adverse immunogenic reactions.

There is, therefore, a need in the art for a radiopharmaceutical which is tumor-specific to neoplastic tissue, and not merely tumor-localizing. Such an agent would not only provide a non-invasive technique for the detection of primary tumors and metastases but would enable monitoring of tumor reduction during therapy.

Some analogues of the naturally-occurring lipid ether, alkyl lysophospholipid, have exhibited an antitumor activity.

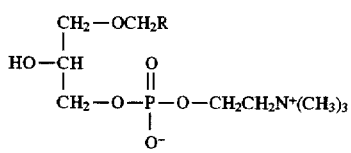

Alkyl Lysophospholipid

The mechanism which underlies this activity is not entirely understood. However, a direct cytotoxic action appears to be involved.

Referring to FIG. 13, a schematic representation of the phospholipid ether catabolic pathway is illustrated. The normal cellular degradation of the ether phospholipid, 1-alkyl-2-acyl-sn-glycero-3-phosphocholine involves deacylation by phospholipase A$_2$ in the 2-position to yield alkyl lysophospholipid. This is followed by the cleavage of the ether bond by the 1-O-alkyl cleavage enzyme to afford sn-glycero-3-phosphocholine. An alternative degradative pathway of alkyl lysophospholipid involves the removal of the phosphocholine moiety. This occurs by the sequential actions of lysophospholipase D and a phosphohydrolase and yields a metabolite of alkyl lysophospholipid, 1-O-alkyl glycerol. Further degradation of this alkyl glycerol requires the 1-O-alkyl cleavage enzyme.

It is proposed that the alkyl lysophospholipid analogues accumulate in tumor cells, thus altering the natural phospholipid metabolism, and are cytotoxic, resulting in cell death. This accumulation is partially attributed to a decrease in activity of the 1-O-alkyl cleavage enzyme which is responsible for cleavage of the ether bond. Reduction in the enzyme's activity retards degradation of the lipids and results in an accumulation of endogenous ether lipids in the tumors. It would be advantageous to develop analogues of the naturally-occurring alkyl lysophospholipid which can be rendered radioactive, will be stable once radiolabelled, and will accumulate specifically in neoplastic tumor tissue.

It is, therefore, an object of this invention to provide a radiopharmaceutical for gamma camera scintigraphy.

It is another object of this invention to provide a radiopharmaceutical for selective visualization of neoplastic lesions.

It is also an object of this invention to provide a radiopharmaceutical which represents an improvement over currently available agents, such as gallium-67 citrate, in that it is tumor-specific versus tumor-localizing.

It is a further object of this invention to provide a radiopharmaceutical such that its radioactivity distribution will not be altered by the action of other drugs, such as steroids and antineoplasts, and therefore can be used to monitor tumor reduction during therapy.

It is additionally an object of this invention to provide a non-invasive technique for detection of primary tumors and metastases.

It is yet a further object of this invention to provide a radiolabelled compound which is similar to platelet activating factor and can be used as a biological probe to study the metabolism of platelet activating factor.

It is also another object of this invention to provide a radiopharmaceutical which is selective to neoplastic tissue, but which is non-specific as to type of neoplastic tissue as are prior art monoclonal antibodies.

It is yet an additional object of this invention to provide a radiopharmaceutical which is non-immunogenic.

It is still another object of this invention to provide a radiopharmaceutical which is not complex in structure and is easily and inexpensively synthesized.

It is a yet further object of this invention to provide a radiopharmaceutical which is cytotoxic for therapeutic purposes.

It is still a further object of this invention to provide a radiopharmaceutical which is useful for radiotherapy.

SUMMARY OF THE INVENTION

The foregoing and other objects are achieved by this invention which provides novel radioiodinated aralkyl phospholipid ether analogues of naturally-occurring phospholipid ether compounds of the general Formula I:

$$\text{X-C}_6\text{H}_4\text{-(CH}_2)_n\text{-O-CH}_2\text{-CH(Y)-CH}_2\text{-O-P(O)(OH)-O-CH}_2\text{-CH}_2\text{-Z}$$

where X is a radioactive isotope of iodine, in certain embodiments of the invention, these isotopes may include $^{123}$I, $^{125}$I, and $^{131}$I; n is an integer between 1 and 15; Y is selected from the group of H, OH, $$\overset{O}{\underset{}{\|}}\text{OCR,}$$

and OR wherein R is an alkyl or aralkyl substituent; and Z is selected from the group of $NH_2$, $NR_2$, and $NR_3$, wherein R is an alkyl or aralkyl substituent.

In accordance with a method aspect of the invention, a physiologically effective amount of the inventive compound is administered to the body of a living being.

In accordance with an inventive use aspect of the invention, the compound having the aforementioned general formula is utilized as a tumor-specific radioactive tracer compound. In an illustrative embodiment, the radioisotope of iodine is selected from the group of $^{123}$I, $^{125}$I, and $^{131}$I. An effective amount of the radioactive tracer compound is administered to the body of the living being so as to cause sufficient gamma rays to be emitted for imaging of neoplastic tissue by gamma-camera scintigraphy.

In accordance with a specific illustrative embodiment of the invention, the inventive compound is 1-[12-(m-iodophenyl)-dodecyl]-2-methyl-rac-glycero-3-phosphocholine.

$$\begin{array}{l}\text{CH}_2-\text{O}-(\text{CH}_2)_{12}-\\|\\\text{HO}-\text{CH} \quad\quad \overset{O}{\underset{}{\|}}\\|\\\text{CH}_2-\text{O}-\text{P}-\text{O}-\text{CH}_2\text{CH}_2\text{N}^+(\text{CH}_3)_3\\\quad\quad\quad |\\\quad\quad\quad \text{O}^-\end{array}$$

1-[12-(m-IODOPHENYL)-DODECYL]-2-METHYL-rac-GLYCERO-3-PHOSPHOCHOLINE (ET-12IP-OME)

In a still further embodiment, the inventive compound is 1-[12-(m-iodophenyl)-dodecyl]-propanediol-3-phosphocholine.

$$\begin{array}{l}\text{CH}_2-\text{O}-(\text{CH}_2)_{12}-\\|\\\text{CH}_2 \quad\quad \overset{O}{\underset{}{\|}}\\|\\\text{CH}_2-\text{O}-\text{P}-\text{O}-\text{CH}_2\text{CH}_2\text{N}^+(\text{CH}_3)_3\\\quad\quad\quad |\\\quad\quad\quad \text{O}^-\end{array}$$

1-[12-(m-IODOPHENYL)-DODECYL]-PROPANEDIOL-3-PHOSPHOCHOLINE (ET-12IP-H)

An alternative embodiment of the invention provides novel radioiodinated aralkyl phospholipid ether analogues of naturally-occurring phospholipid ether compounds of the general Formula II:

$$\text{CH}_3(\text{CH}_2)_n-\text{O-CH}_2-\text{CH(X)-CH}_2-\text{O-P(O)(OH)-O-CH}_2-\text{CH}_2-\text{Y}$$

where n=1–15

$$X = \text{OC}(=\text{O})-(\text{CH}_2)_m-\text{C}_6\text{H}_4-\text{Z}$$

or:

$$X = \text{O-CH}_2-(\text{CH}_2)_m-\text{C}_6\text{H}_4-\text{Z}$$

m=0–15
Z=$^{123}$I, $^{125}$I, and $^{131}$I
Y=$NH_2$, $NR_2$, and $NR_3$
R=alkyl, aralkyl In accordance with another embodiment of the invention, the monoiodinated aralkyl side chain may be substituted directly onto alkyl phosphocholine moiety in accordance with general Formula III:

$$\text{Y-CH}_2-\text{CH}_2-\text{O}-\overset{O}{\underset{|}{\overset{\|}{\text{P}}}}-\text{O-X}$$
$$\quad\quad\quad\quad\quad\quad\quad\quad \text{OH}$$

where

Y=NH$_2$, NR$_2$, NR$_3$, NR$_2$R'
R=alkyl, aralkyl
R'=a monoiodinated aralkyl, such as

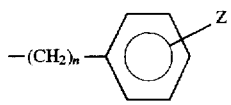

z=$^{122}$I, $^{123}$I, $^{125}$I, and $^{131}$I
n=1–15

X=a monoiodinated aralkyl, like R', where n=1–15; or an alkyl, such as —CH$_2$—(CH$_2$)$_m$—CH$_3$, where m=1–15
Provided, however, that one, and only one, of X or Y is a monoiodinated aralkyl.

The resulting analogues of alkyl phosphocholine have less complex structures and are simpler and less expensive to prepare than the analogues of alkyl lysophospholipids of general Formulas I and II.

In accordance with a specific illustrative embodiment of the invention, the inventive compound is 12-(m-iodophenyl)-dodecyl phosphocholine.

In accordance with yet a further specific illustrative embodiment of the invention, the inventive compound is hexadecyl-2-[N,N,-dimethyl-N-(m-iodobenzyl)-ammonium] ethylphosphate.

BRIEF DESCRIPTION OF THE DRAWING

Comprehension of the invention is facilitated by reading the following detailed description in conjunction with the annexed drawing, in which:

FIG. 18 is a bar graph showing tissue distribution of radioiodinated 12-(m-iodophenyl)-dodecyl phosphocholine in nude mice bearing HTB 63 human melanoma tumors at 13 days post-injection.

DETAILED DESCRIPTION

The following examples relate to specific embodiments of the radioiodinated phospholipid analogues of the present invention, and include illustrative methods for synthesizing the analogues.

Figure 1:
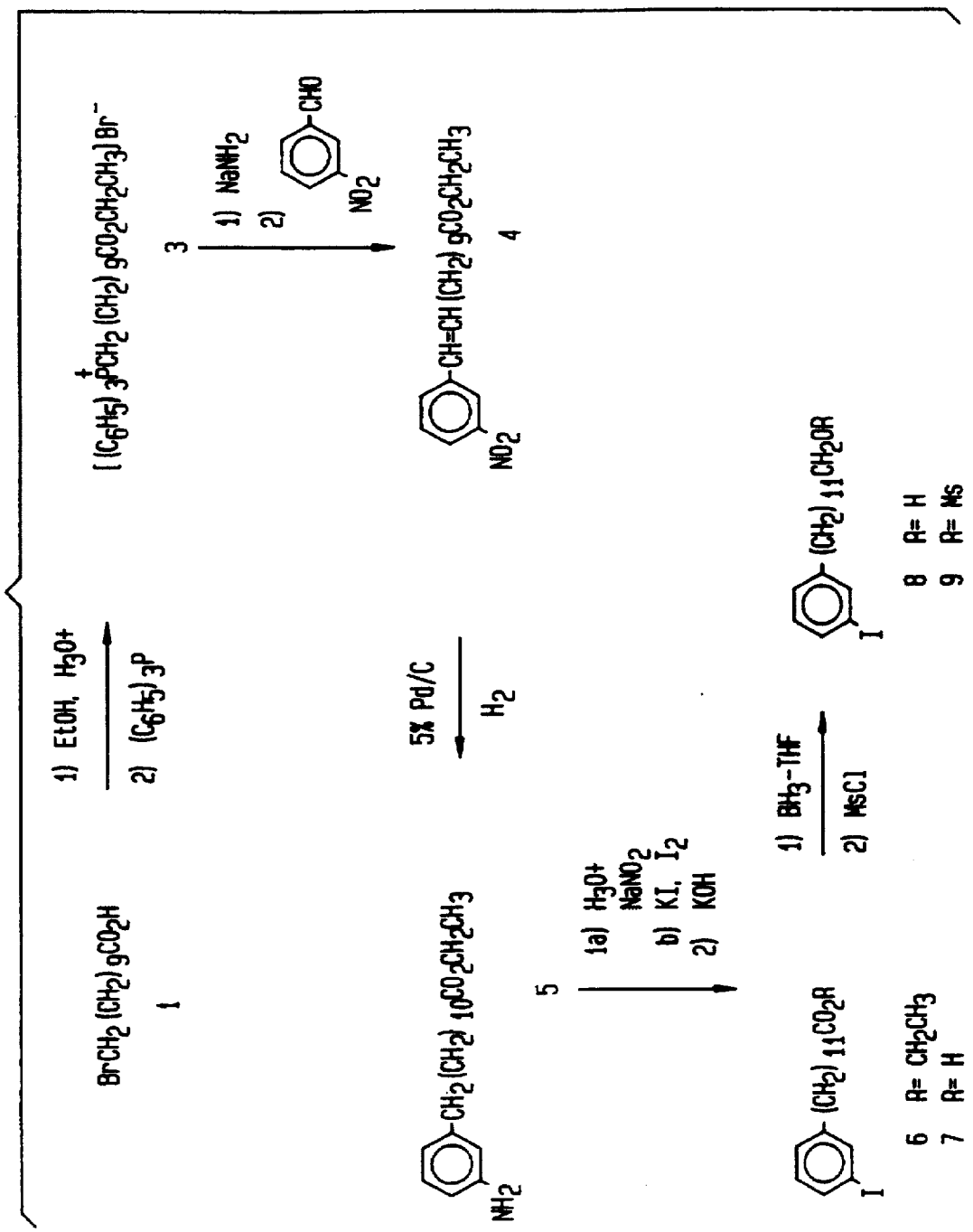
FIG. 1 is an illustrative preparatory scheme for 12-(m-iodophenyl)-dodecyl methane sulfonate.

Alkyl Lysophospholipid Analogues
Example 1:

The synthesis of 12-(m-iodophenyl)-dodecyl methane sulfonate, a necessary compound for the illustrative preparatory schemes for the phospholipid ether analogues discussed in detail in Examples 2 and 3 hereinbelow, was accomplished from 11-bromoundecanoic acid in accordance with the illustrative preparatory scheme shown in FIG. 1.

In general terms, the scheme comprises: esterification of 11-bromoundecanoic acid (compound 1) followed by reaction with triphenylphosphine to yield the corresponding phosphonium salt (compound 3). A Wittig reaction involving compound 3 with m-nitrobenzaldehyde afforded m-nitrophenyl alkenoate (compound 4) which, upon subsequent catalytic hydrogenation gave rise to an m-aminophenyl alkanoate (compound 5). The m-aminophenyl alkanoate was converted to the corresponding diazonium salt and the diazonium ion was subsequently displaced by iodide to afford ester (compound 6). The ester was saponified, reduced to the corresponding acid (compound 7) and the resulting alcohol compound 8 was mesylated to form the mesylate compound 9.

Compound 1, 11-Bromoundecanoic acid (41.38 g, 156 mmol), was placed in a 250 ml round-bottomed flask equipped with a reflux condenser. After absolute ethanol (60 ml) and concentrated HCl (½ ml) were added, the reaction mixture was refluxed overnight. The reaction mixture was allowed to cool to room temperature before the solvent was removed under reduced pressure. The resulting yellow oil was dissolved in ether. The ether solution was extracted with saturated sodium carbonate (NaHCO$_3$) and H$_2$O, and dried over magnesium sulfate (MgSO$_4$). The solvent was removed under reduced pressure. Purification of the crude product was obtained by vacuum distillation which yielded a colorless oil, ethyl-11-bromoundecanoate, compound 2 (37.32 g, 82.5% yield).

Ethyl-11-bromoundecanoate (36.0 g, 123 mmol) and acetonitrile (200 ml) were placed in a flame-dried three-neck 500 ml round-bottomed flask equipped with a reflux condenser. Triphenyl phosphine (35.5 g, 135 mmol) was added to the solution and the reaction mixture was refluxed for 36 hours under anhydrous conditions. After the reaction mixture had cooled to room temperature, the acetonitrile was removed under reduced pressure. The crude product was triturated with ether. The solid was filtered and washed with ether to yield a pure compound 3, 11-carbethoxyundecyltriphenylphosphonium bromide (56.69 g, 83% yield).

Sodium amide (0.40 g, 9.74 mmol) was weighed directly into a flame-dried 50 ml round-bottomed flask filled with argon. 11-Carbethoxyundecyltriphenylphosphonium bromide (5.00 g, 9.0 mmol) was added followed by anhydrous tetrahydrofuran (THF, 15 ml). The mixture was cooled to −30° C. After the reaction mixture had stirred for 30 minutes at −30° C., a solution of m-nitrobenzaldehyde (1.4 g, 9.30 mmol) in anhydrous THF (5 ml) was added dropwise. The reaction mixture was allowed to warm to room temperature and was stirred for 4 hours. Ether was added. The reaction mixture was cooled to 0° C., and $H_2O$ was cautiously added to destroy residual base. The ether layer was removed, washed with $H_2O$, 2% $NaHSO_4$ and brine, and dried ($MgSO_4$). The solvent was evaporated under reduced pressure to yield an oily residue. Purification by column chromatography (150 g silica gel, hexanes:ethyl acetate, 15:1) gave the pure compound 4, ethyl-12-(m-nitrophenyl)-11-dodecenoate (1.323 g, 42% yield).

Ethyl-12-(m-nitrophenyl)-11-dodecanoate (9.76 g, 28.1 mmol) was dissolved in ethyl acetate (55 ml). The solution was hydrogenated over 5% Pd/C (0.346 g) at room temperature and at an initial pressure of 45 psi for four hours. The reaction mixture was filtered through Celite and the solvent was removed under reduced pressure to yield an oily residue. The crude product was purified by column chromatography (80 g silica gel, hexanes:ethyl acetate, discontinuous gradient 10:1–2:1) to yield the reduced compound 5, ethyl-12-(m-aminophenyl)-dodecanoate (8.75 g, 97.5% yield).

Glacial acetic acid (4 ml) and concentrated HCl (2.5 ml) were added to a 50 ml Erlenmeyer flask containing ethyl-12-(m-amino-phenyl)-dodecanoate (3.92 g, 12.28 mmol). The mixture was cooled in a Nacl/ice bath. A cold aqueous solution of $NaNO_2$ (4 ml, 3.1 M) was added to the mixture. The reaction was stirred for 40 minutes before a cold aqueous solution of $KI/I_2$ (2.31/1.78 g, 7 ml) was added. The reaction mixture was allowed to warm to room temperature and was stirred overnight. Ether was added to the reaction mixture. The ether layer was separated and extracted with $H_2O$, 10% $Na_2S_2O_3$, $H_2O$, sat. $NaHCO_3$, and brine. The organic layer was dried ($MgSO_4$) and the solvent removed under reduced pressure to give a reddish oil. The crude product was purified by column chromatography (120 g silica gel, hexanes:ethyl acetate 20:1) to yield a clear oil, compound 6, ethyl-12-(m-iodophenyl)-dodecanoate (5.28 g, 56.8% yield).

Ethyl-12-(m-iodophenyl)-dodecanoate (7.17 g, 16.67 mmol), 95% ethanol (100 ml) and KOH (2.0 g) were placed into a 250 ml round-bottomed flask fitted with a reflux condenser. The reaction mixture was refluxed overnight. The ethanol was removed in vacuo and $H_2O$ was added. The aqueous solution was acidified and then extracted with ether. The ether layer was dried ($MgSO_4$), and the solvent was evaporated to yield a yellow solid. The crude product was recrystallized with 95% ethanol to provide a white flaky solid, compound 7, 12-m-iodophenyldodecanoic acid (5.9 g, 88.0% yield).

Anhydrous THF (20 ml) was added to a flame-dried 100 ml two-necked flask containing 12-m-iodophenyldodecanoic acid (3.30 g, 8.21 mmol). The solution was cooled in an ice bath before $BH_3$-THF (15.0 ml, 1M) was added dropwise. The reaction mixture was allowed to warm to room temperature and to stir under anhydrous conditions for 20 hours. The reaction mixture was again cooled to 0° C. and quenched with $H_2O$. Ether and additional $H_2O$ were then added. The ether layer was extracted with $H_2O$, sat. $NaHCO_3$, and more $H_2O$ and dried ($MgSO_4$). The solvent was removed under reduced pressure to yield a yellow oil. The crude compound was purified by column chromatography (90 g silica gel, hexanes:ethyl acetate 8:1) to yield a white solid, compound 8, 12-m-iodophenyldodecanol (3.14 g, 98.4% yield).

12-m-Iodophenyldodecanol (5.88 g, 15.17 mmol) was placed into a flame-dried three-neck 100 ml round-bottomed flask equipped with a reflux condenser and charged with $N_2$. Anhydrous pyridine (30 ml) was added. The mixture was cooled to 0° C. before freshly distilled methane sulfonyl chloride (2.0 ml, 25.96 mmol) was added dropwise. The reaction mixture was allowed to warm to room temperature. After the reaction mixture had been stirred for several hours, it was poured into ice cold $H_2O$ and the resulting precipitate was filtered. The solid was dissolved in ether and extracted with $H_2O$, 1N HCl, and $H_2O$. The ether layer was dried ($MgSO_4$) and the solvent was evaporated in vacuo. The crude product was recrystallized with a hexanes and ethyl acetate mixture to yield the pure mesylate, compound 9, 12-(m-iodophenyl)-dodecyl methanesulfonate (4.95 g, 70.7%).

Figure 2:
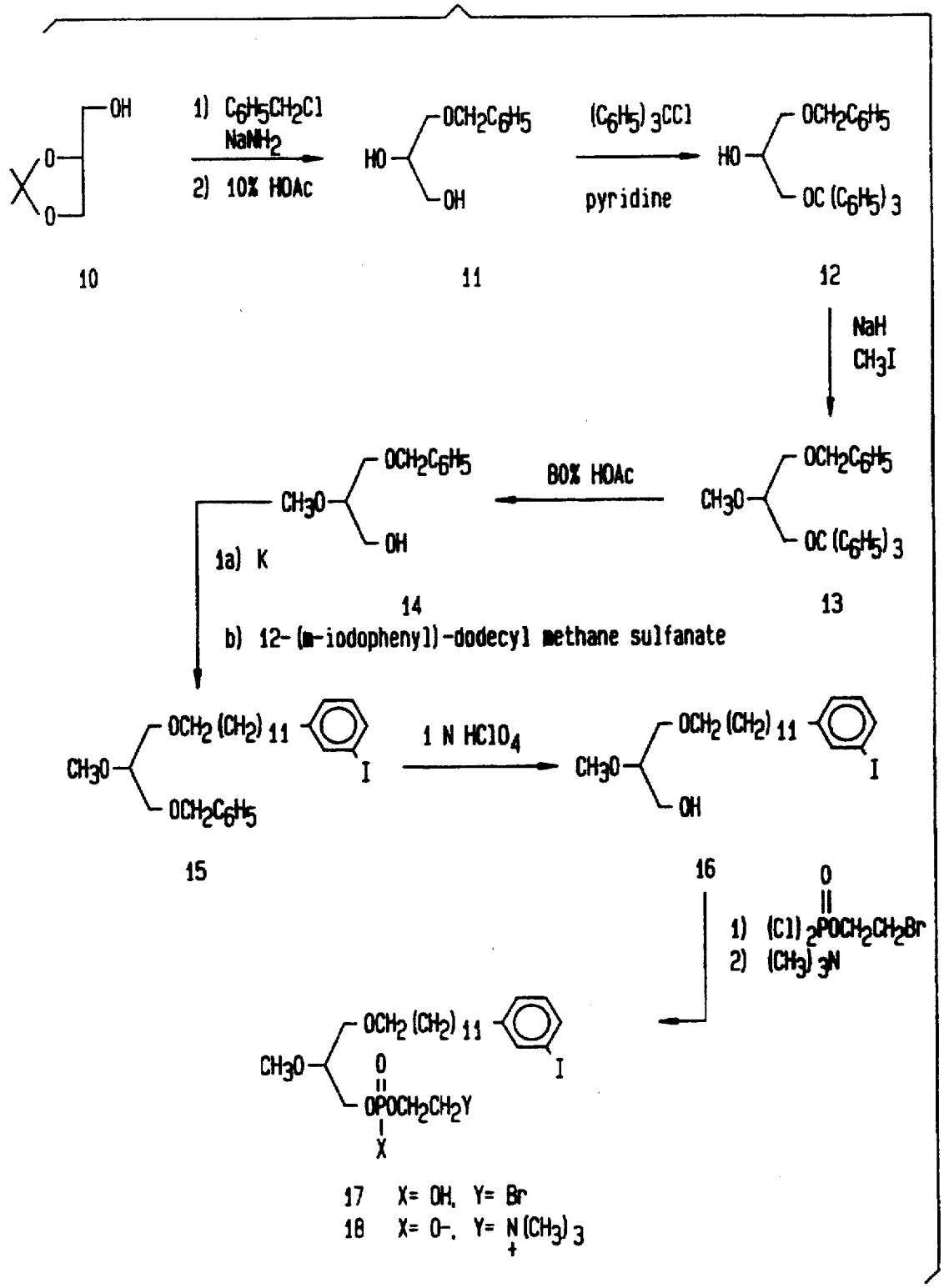
FIG. 2 is an illustrative preparatory scheme for 1-[12-(m-iodophenyl)-dodecyl]-2-methyl-rac-glycero-3-phosphocholine.

Example 2:

In a specific illustrative embodiment of a phospholipid ether analogue in accordance with the present invention, the synthesis of 1-[12-(m-iodophenyl)-dodecyl]-2-methyl-rac-glycero-3-phosphocholine was accomplished according to the illustrative preparatory scheme shown in FIG. 2.

Etherification of rac-1-benzyl-2-methyl glycerol (compound-14) with the sulfonate of Example 1 (compound 9, FIG. 1) was a necessary step. rac-1-Benzyl-2-methyl glycerol was prepared from rac-isopropylidene glycerol (compound 10). Following etherification of rac-1-benzyl-2-methyl glycerol, debenzylation was accomplished under acidic conditions to yield alcohol compound 16. Condensation of alcohol 16 with 2 bromoethyl phosphoryl dichloride afforded compound 17 which upon treatment with trimethyl amine yielded 1-[12-(m-iodophenyl)-dodecyl]-2-methyl-rac-glycero-3-phosphocholine (compound 18).

Referring to FIG. 2, the preparation of 1-[12-(m-iodophenyl)-dodecyl]-2-methyl-rac-glycero-3-phosphocholine is described in detail. Isopropylidene glycerol (21.3 g, 161 mmol) was added dropwise into a flame-dried three-necked 200 ml round-bottomed flask containing anhydrous benzene (50 ml) and $NaNH_2$ (6.62 g, 161 mmol) which was equipped with a reflux condenser. The reaction mixture was refluxed under anhydrous conditions for one hour before benzyl chloride (24.0 g, 193 mmol) was slowly added to the hot mixture. The reaction mixture was refluxed overnight. After the reaction mixture had cooled to room temperature, $H_2O$ was cautiously added. The benzene layer was removed and washed several times with $H_2O$ and dried ($MgSO_4$). The solvent was removed in vacuo to give a dark brown oil which was purified by vacuum distillation to yield pure benzyl ether, rac-1-O-benzyl-2,3-O-isopropylidine glycerol (23.1 g, 79%).

rac-1-O-Benzyl-2,3-O-isopropylidine glycerol (26.8 g, 121 mmol) and 10% HOAc (55 ml) were placed in a 200 ml round-bottomed flask fitted with a reflux condenser. The reaction mixture was refluxed for 4 hours before the solvent was removed by distillation. The residual pale yellow oil was vacuum distilled to yield the pure diol, compound 11, rac-1-O-benzylglycerol (18.2 g, 82.7%).

rac-1-O-Benzylglycerol (5.37 g, 29.5 mmol), trityl chloride (8.31 g, 29.8 mmol) and anhydrous pyridine (35 ml) were placed in a flame-dried 200 ml round-bottomed flask. The reaction mixture was stirred under anhydrous conditions at room temperature for two days. The precipitate which formed was filtered before $H_2O$ and ether were added. The ether layer was extracted with $H_2O$, 1N HCl and $H_2O$, and dried ($MgSO_4$). The solvent was removed by reduced pressure to provide a viscous yellow oil. The crude product was purified by column chromatography (180 g silica gel; hexanes:ethyl acetate, gradient 8:1 to 3:1) to yield pure compound 12, rac-1-O-benzyl-3-O-tritylglycerol (9.00 g, 72% yield).

Method A (not shown in FIG. 2)

$NaNH_2$ (0.616 g, 15.0 mmol) was added to a flame-dried two-necked 50 ml round bottom flask equipped with a reflux condenser which contained a solution of rac-1-O-benzyl-3-O-tritylglycerol (5.30 g, 12.5 mmol) in anhydrous 1,4 dioxane (30 ml). The reaction mixture was refluxed for one hour under $N_2$. Then $CH_3I$ (3.55 g, 25.0 mmol) was added dropwise. The resulting reaction mixture was refluxed overnight. After the mixture had cooled to room temperature, ether and $H_2O$ were added. The ether layer was removed and extracted with 1N HCl, $H_2O$, sat. $NaHCO_3$, $H_2O$, and brine. The organic layer was dried ($MgSO_4$) and the solvent was removed in vacuo to give a yellow oil which solidified upon standing. The crude solid was recrystallized with hexanes to yield pure compound 13, rac-1-O-benzyl-2-O-methyl-3-O-tritylglycerol (4.32 g, 78.9%).

Method B

Anhydrous THF (30 ml) and NaH (0.467 g, 19.45 mmol) were added to a flame-dried three-necked 200 ml round-bottomed flask equipped with a reflux condenser. This mixture was heated to 55° C. before $CH_3I$ (1.7 ml, 27.07 mmol) was added dropwise. A solution of rac-1-O-benzyl-3-O-tritylglycerol (6.60 g, 15.56 mmol) in anhydrous THF (20 ml) was then added slowly. After the reaction mixture had been stirred for four hours at 55° C., the heat was removed and the reaction mixture was cooled to 0° C. $H_2O$ was cautiously added. The solvent was removed in vacuo. The residue was dissolved in ether and the solution was extracted twice with $H_2O$. The ether solution was dried ($MgSO_4$) and the solvent was removed under reduced pressure to yield the crude product, compound 13 (6.73 g). The crude product from this method was not purified, but used directly in the next reaction.

rac-1-O-Benzyl-2-O-methyl-3-O-tritylglycerol (6.73 g) and 80% HOAc (50 ml) were combined in a 100 ml flask and heated at reflux for three hours. The heat was removed and the reaction mixture was allowed to cool to room temperature. The reaction was neutralized with 10% KOH and extracted with ether. The ether layer was dried ($MgSO_4$) before the solvent was removed in vacuo. Purification of the residue was obtained by column chromatography (150 ml silica gel; hexanes:ethyl acetate, gradient 5:1–0:1). The pure compound 14, rac-1-O-benzyl-2-O-methylglycerol, was obtained as a clear oil (1.84 g, 59.7% yield).

Anhydrous benzene (5 ml) and potassium metal (0.748 g, 1.91 mmol) were added to a flame-dried three-neck 50 ml round-bottomed flask equipped with a reflux condenser under a $N_2$ atmosphere. The mixture was heated to reflux. After the potassium metal had melted, a solution of rac-1-O-benzyl-2-O-methylglycerol (0.423 g, 2.15 mmol) in anhydrous benzene (5 ml) was added dropwise via a syringe. The reaction mixture was allowed to reflux for one hour before a solution of 12-(m-iodophenyl)-dodecyl methanesulfonate (0.868 g, 1.86 mmol) in dry benzene (4 ml) was added. The 12-(m-iodophenyl)-dodecyl methanesulfonate was produced in the reaction scheme of Example 1 and FIG. 1 discussed in detail hereinabove. The reaction mixture was refluxed overnight and the reaction mixture was cooled to 0° C. before $H_2O$ was slowly added. The organic layer was separated, extracted with $H_2O$, 1N $H_2SO_4$, and $H_2O$ and then dried ($MgSO_4$). The removal of the solvent under reduced pressure provided the crude product which was purified by column chromatography (26 g silica gel, hexanes:ethyl acetate, 8:1) to yield the pure ether, compound 15, rac-1-O-|12-(m-iodophenyl)-dodecyl]-2-O-methyl-3-O-benzylglycerol (349 mg, 33% yield).

rac-1-O-|12-(m-Iodophenyl)-dodecyl|-2-O-methyl-3-O-benzyl-glycerol (840 mg, 1.48 mmol) and a 1N solution of $HClO_4$ in dioxane (11 ml) were combined in a 25 ml round-bottomed flask equipped with a reflux condenser. The reaction mixture was heated at 80°–100° C. for ten hours. The heat was removed and the reaction mixture was allowed to cool to room temperature. The solvent was removed in vacuo. Ether was added and the solution was extracted with $H_2O$, sat. $NaHCO_3$ and $H_2O$. After the organic layer was dried ($MgSO_4$), the solvent was removed under reduced pressure to yield the crude product which was purified by column chromatography (90 g silica gel; hexanes:ethyl acetate 4:1) to obtain pure alcohol compound 16, rac-1-O-[12-(m-iodophenyl)-2-O-methylglycerol (470 mg, 66% yield).

A solution of 2-bromoethyl dichlorophosphate (0.277 g, 1.14 mmol) in anhydrous ether (7 ml) was placed into a flame-dried, three neck 50 ml round-bottomed flask which was equipped with a reflux condenser and charged with $N_2$. The solution was cooled to 0° C. before dry pyridine (0.40 ml) was added. A solution of rac-1-O-|12-(m-iodophenyl)-2-O-methylglycerol (150 mg, 0.315 mmol) in anhydrous ether (1.5 ml) was added. The reaction mixture was stirred at 0° C. for 10 minutes before it was heated at a gentle reflux for 4.5 hours. The heat was removed and the reaction mixture was allowed to cool to room temperature before $H_2O$ (½ ml) was added. After the reaction mixture had been stirred for 30 minutes, the solvent was removed in vacuo. The residue was dissolved in chloroform and the solution was extracted with $H_2O$, 1N HCl and $H_2O$. Methanol was used to disrupt the emulsions which formed as an azeotrope with benzene. The crude product was purified by column chromatography (19 g silica gel, chloroform:methanol, 9:1) to obtain the pure compound 17, rac-1-O-[12-(m-iodophenyl)-dodecyl]-2-O-methyl-3-O-(2'-bromoethyl) phosphorylglycerol.

rac-1-O-[12-(m-Iodophenyl)-dodecyl]-2-O-methyl-3-O-(2'-bromoethyl)-phosphorylglycerol (73 mg, 0.110 mmol) and $N(CH_3)_3$ (45–50% aq. solution, 0.80 ml, 5.4 mmol) were added to a three neck round-bottomed flask containing $CHCl_3$:isopropanol:DMF (3:5:5, 6.5 ml). The reaction mixture was heated at 50° C. for 5.5 hours. The heat was removed and the reaction mixture was allowed to cool to room temperature before $Ag_2CO_3$ (39 mg, 0.14 mmol) was added. The heat was then reapplied for 1 hour. The reaction mixture was cooled, filtered, and the solvent removed under reduced pressure. The crude product was purified by column chromatography (14 g silica gel, $CHCl_3:CH_3OH:H_2O$, 65:35:4) to yield the pure phospholipid compound 18, 1-O-|12-(m-iodophenyl)-dodecyl]-2-O-methyl-rac-glycero-3-O-phosphocholine (37 mg, 52.4% yield).

Figure 3:
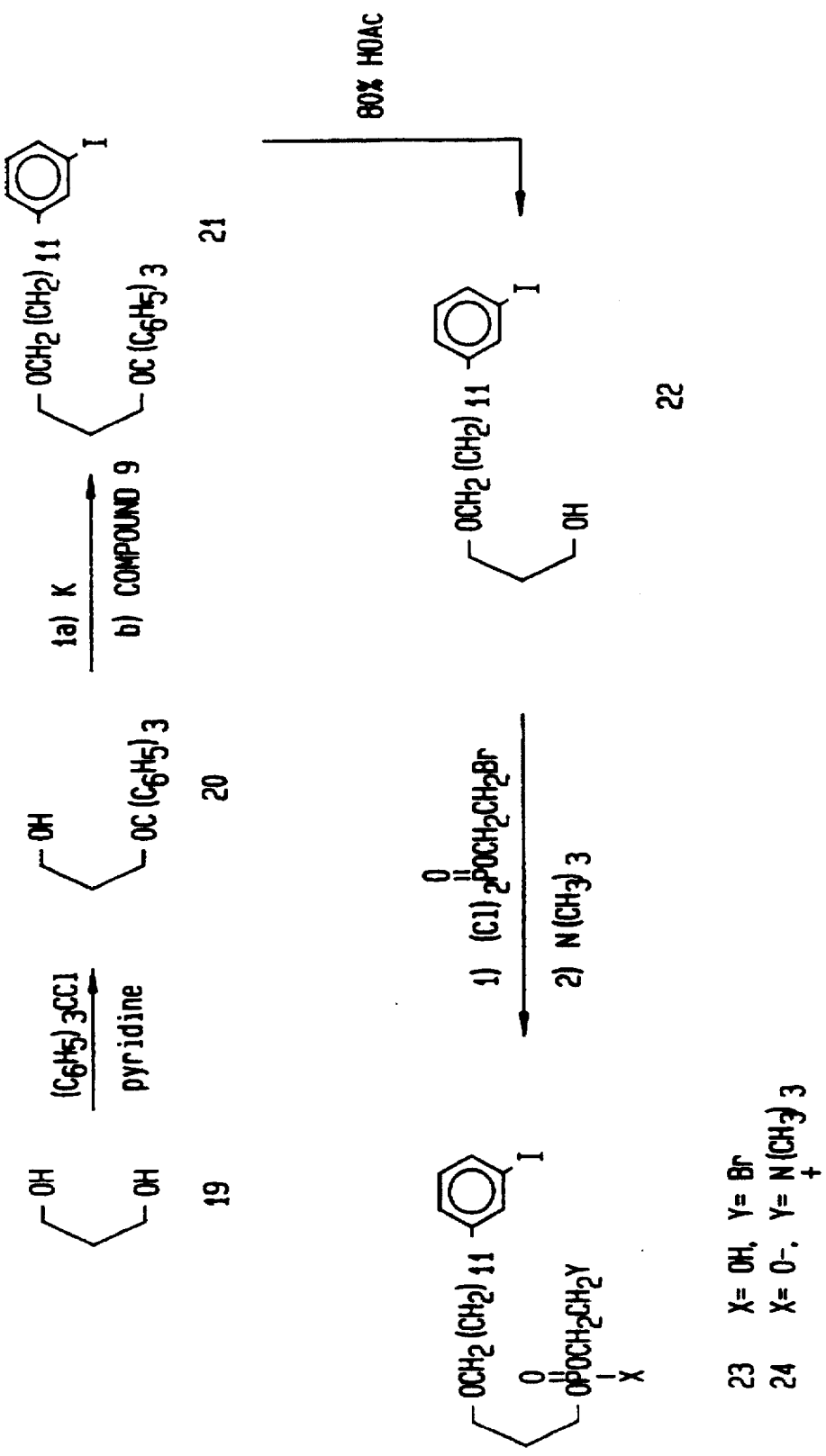
FIG. 3 is an illustrative preparatory scheme for 1-[12-(m-iodophenyl)-dodecyl]-propanediol-3-phosphocholine.

Example 3:

Synthesis of another phospholipid ether analogue within the purview of this invention is shown in the preparatory scheme of FIG.3. 1-|12-(m-Iodophenyl)-dodecyl|-propanediol-3-phosphocholine was prepared by the etherification of 3-trityl propanediol with the methane sulfonate (compound 9) of Example 1 followed by detritylation under acidic conditions to provide alcohol compound 22. The phosphocholine moiety was added to the alcohol in the manner described above with respect to Example 2.

1,3-Propanediol (1.053 g, 13.84 mmol), trityl chloride (3.50 g, 12.6 mmol) and anhydrous pyridine (5 ml) were combined in a flame-dried round-bottomed flask. The reaction mixture was stirred overnight at room temperature. Ether was added to the reaction mixture and the solution was extracted with $H_2O$, 1N HCl, $H_2O$, and brine. The ether layer was dried ($MgSO_4$) and the solvent removed under reduced pressure. The crude product was purified by column chromatography (100 g silica gel; hexanes:ethyl acetate, gradient 8:1 to 6:1) to provide the pure ether compound 20, 1-O-trityloxy-propanol (1.85 g, 46.4% yield).

Anhydrous THF (3 ml) and $NaNH_2$ (95%, 0.057 g, 1.38 mmol) were placed into a flame-dried three-necked round-bottomed flask. A solution of 1-O-trityloxy-propanol (0.347 g, 1.09 mmol) in THF (2.5 ml) was slowly added to the reaction mixture. The reaction mixture was heated to reflux for 1.5 hours before a solution of 12-(m-iodophenyl)-dodecyl methanesulfonate (compound 9; 0.508 g, 1.09 mmol) in THF (2.5 ml) was added slowly to the reaction mixture. The resulting reaction mixture was heated to reflux overnight. Additional $NaNH_2$ (95%, 0.058 g, 1.49 mmol) was added and the reaction mixture was again heated to reflux for 5 hours. The heat was removed and the reaction mixture was allowed to cool to room temperature before $H_2O$ was cautiously added to destroy residual base. The solvent was removed under reduced pressure. The residue was dissolved into ether and extracted with $H_2O$. The ether layer was dried ($MgSO_4$) and the solvent removed. The crude product was purified by column chromatography (35 g silica gel; hexanes:ethyl acetate, 15:1) to yield the pure ether compound 21, 1-O-[12-(m-iodophenyl)-dodecyl]-3-O-trityl propanediol (325 mg, 44.6%).

1-O-[12-(m-iodophenyl)-dodecyl]-3-O-trityl propanediol (370 mg, 0.554 mmol), 95% ethanol (20 ml), and concentrated $H_2SO_4$ (5 drops) were combined in a 50 ml round bottom flask equipped with a reflux condenser. The reaction mixture was warmed to 60° C. overnight. The solvent was removed under reduced pressure before ether and water were added. The organic layer was removed, extracted with saturated $NaHCO_3$, $H_2O$, 1N $H_2SO_4$, and $H_2O$, and then dried ($MgSO_4$). The solvent was removed under reduced pressure. The crude product was purified by column chromatography (13 g silica gel; hexanes:ethyl acetate, gradient 6:1 to 4:1) to yield alcohol 22, 1-O-[12-(m-iodophenyl)-dodecyl]-3-propanediol (88 mg, 35.6% yield).

A solution of 2-bromoethyl dichlorophosphate (0.274 g, 1.13 mmol) in anhydrous ether (5 ml) was placed in a flame-dried round bottom flask equipped with a reflux condenser. The solution was cooled to 0° C. before dry pyridine (0.40 ml) was added. A solution of 1-O-[12-(m-iodophenyl)-dodecyl]-3-propanediol (141 mg, 0.316 mmol) in anhydrous ether (4 ml) was added. The reaction mixture was stirred at 0° C. for 10 minutes and then heated to reflux for 3 hours. The heat was removed and the reaction mixture was allowed to cool to room temperature before $H_2O$ (0.50 ml) was added. After the reaction mixture had been stirred for 30 minutes, the solvent was removed in vacuo. The residue was dissolved in $CHCl_3$ and the solution was extracted with $H_2O$, 1N HCl and H2O. Methanol was used to disrupt the emulsion which formed. The solvent was removed in vacuo and the residual $H_2O$ was removed as an azeotrope with benzene. The crude product was purified by column chromatography (30 g silica gel, $CHCl_3:CH_3OH$, 12:1) to obtain the pure compound 23, 1-O-|12-(m-iodophenyl)-dodecyl]-3-(2'-bromoethyl)-phosphoryl (100 mg, 50.3% yield).

1-|12-m-(Iodophenyl)-dodecyl|-3-(2' bromoethyl)-phosphoryl propane (37 mg, 0.058 mmol) and $N(CH_3)_3$ (45–50% aq. solution, 0.40 ml, 2.63 mmol) were added to a two-necked pear-shaped flask containing $CHCl_3$:isopropanol:DMF (3:5:5, 3.75 ml). The reaction mixture was heated at 50° C. for 6.5 hours. The heat was removed and the reaction mixture was allowed to cool to room temperature before $Ag_2CO_3$ (21 mg, 0.076 mmol) was added. The heat was reapplied for 1 hour. The reaction mixture was cooled, filtered, and the solvent removed under reduced pressure. The crude product was purified by column chromatography (10 g silica gel, $CHCl_3:CH_3OH:H_2O$, 65:25:4) to yield the pure compound 24, 1-O-|12-(m-iodophenyl)-dodecyl|-propanediol-3-O-phosphocholine (17 mg, 47% yield).

Radioiodination of the Phospholipid Ether Analogues

For certain uses, such as scintigraphy or experimental evaluation of tissue distribution, it is desirable to create radioactive compounds. Radioiodination of the iodinated phospholipid ether analogues disclosed herein, or one of the intermediates in the synthesis pathway, such as a trityl-protected compound, can be accomplished by a variety of techniques, some of which are known in the art. For example, aromatic compounds with electron donating groups (such as anilines) can be radiolabelled by electrophilic iodination in the presence of radioiodine, iodine monochloride, chloramine-T, iodogen, etc. Unactivated aromatic rings, can be radioiodinated by exchange of a leaving group, such as aryl boronic acids, aryl thallium trifluoroacetates, triazenes or metallated arenes with radioiodine. Direct electrophilic radioiodination of a phenyl ring is yet another alternative, but may produce isomeric mixtures which are difficult to separate. Iodine exchange of aryl iodides with radioiodine may be a preferable approach insofar as no complex separation techniques are necessary since the substrate and radioiodinated product are chemically identical.

In a preferred embodiment of the invention, an isotopes exchange-type technique is utilized wherein the substrate and radioiodine are reacted at an elevated temperature in a "melt." The molten reaction medium possesses a sufficiently high dielectric constant to solubilize both the substrate and radioiodide. Examples of reaction media currently in use are benzoic acid (mp 122° C., bp 249° C.) and acetamide (mp 82° C., bp 221° C.). In a specific preferred embodiment, an acidic exchange medium comprising pivalic acid, a homolog of acetic acid, also known as trimethyl acetic acid, can be used. Pivalic acid has a melting point of 33° C. and a boiling point of 164° C.

The phospholipid ether analogue (1 mg) and pivalic acid (10 mg) were placed in a 1 ml serum vial. The vial was flushed with $N_2$ and sealed with a teflon-lined rubber septum and aluminum cap. Aqueous $Na^{125}I$ (0.5–1.0 μL, 100–500 μCi) was added. A stream of $N_2$ was used to remove the water and the reaction mixture was then heated at 150° C. for 30 minutes. The reaction mixture was allowed to cool to room temperature before extraction with a chloroform:methanol mixture (1:2 volume ratio, 60 µL) and water (60 µL). The organic layer was removed and added to a silica gel-60 column (1×5 cm). The column was initially eluted with chloroform:methanol (1:1) to remove the $Na^{125}I$ and then with chloroform:methanol:water (65:25:4) to obtain the radioiodinated product.

Of course, any isotope of iodine such as the clinically used isotopes, $^{122}I$, $^{123}I$, $^{125}I$ and $^{131}I$ can be used. $^{125}I$ is preferred for in vitro work in the laboratory due to its relatively long half-life. For radiodiagnostic purposes in humans, $^{123}I$ or $^{131}I$ are preferred due to their shorter half-lives. The advent of positron emission tomography has also created a use for the positron-emitting $^{122}I$ isotope. The radioiodination procedures may be modified, as known by those of skill in the art, to compensate for the difference in half-life.

The above-described radioiodinated phospholipid ether analogues may be solubilized in a suitable transport agent, or carrier vehicle, and administered to mammalian subjects as radiologic agents by any known manner, preferably intraparentally such as intravenously or intraperitonally.

Tissue Distribution Studies

Radiolabelled compounds 1-[12-(m-iodophenyl)-dodecyl]-2-methyl-rac-glycero-3-phosphocholine (ET-12IP-OMe; Example 2, compound 18) and 1-[12-(m-iodophenyl)-dodecyl]-propanediol-3-phosphocholine (ET-12IP-OH; Example 3, compound 24) were prepared and administered to two sets of female Sprague Dawley rats: normal rats (control) and rats bearing tumors resulting from Walker 256 sarcoma cells which had been implanted into the thigh. The labelled compounds (5–35 µCi $^{125}I$) were administered intravenously in a 2% Tween 20-saline vehicle. At various times following administration the animals were sacrificed, and selected tissue samples were removed. The tissue samples were weighed and placed in cellulose acetate capsules. The radioactivity was then counted (85% efficiency) using a well scintillation counter (Searle 1185). The results from those tissues with the highest concentration of radioactivity are shown in Tables 1–4 below.

TABLE 1

DISTRIBUTION OF RADIOACTIVITY 6 HOURS AFTER IV ADMINISTRATION OF $^{125}I$-LABELLED ET-12IP-OME IN NORMAL AND TUMOR-BEARING RATS[A,B]

| TISSUE | CONTROL | TUMOR[C] |
|---|---|---|
| BLOOD | 0.105 ± 0.009 | 0.231 ± 0.008 |
| KIDNEY | 0.650 ± 0.114 | 1.315 ± 0.091 |
| LIVER | 1.744 ± 0.125 | 3.588 ± 0.189 |
| LUNG | 0.356 ± 0.012 | 0.873 ± 0.081 |
| MUSCLE | 0.023 ± 0.000 | 0.046 ± 0.001 |
| TUMOR | — | 1.123 ± 0.024 |

[A](% Dose/Gram of Tissue)
[B]N = 3, Mean ± Standard error
[C]Walker 256 Sarcoma Implanted in Thigh

TABLE 2

DISTRIBUTION OF RADIOACTIVITY 24 HOURS AFTER IV ADMINISTRATION OF $^{125}I$-LABELLED ET-12IP-OME IN NORMAL AND TUMOR-BEARING RATS[A]

| TISSUE | CONTROL[B] | TUMOR[C,D] |
|---|---|---|
| BLOOD | 0.085 ± 0.001 | 0.096 ± 0.023 |
| KIDNEY | 0.426 ± 0.030 | 0.463 ± 0.111 |
| LIVER | 0.675 ± 0.020 | 0.743 ± 0.105 |
| LUNG | 0.218 ± 0.010 | 0.299 ± 0.017 |
| MUSCLE | 0.034 ± 0.004 | 0.027 ± 0.006 |
| TUMOR | — | 1.115 ± 0.016 |

[A](% Dose/Gram of Tissue)
[B]N = 4, Mean ± standard error
[C]N = 3, Mean ± standard error
[D]Walker 256 Sarcoma Implanted in Thigh

TABLE 3

DISTRIBUTION OF RADIOACTIVITY 6 HOURS AFTER IV ADMINISTRATION OF $^{125}I$-LABELLED ET-12IP-H IN NORMAL AND TUMOR-BEARING RATS[A,B]

| TISSUE | CONTROL | TUMOR[C] |
|---|---|---|
| BLOOD | 0.475 ± 0.078 | 0.239 ± 0.024 |
| KIDNEY | 2.599 ± 0.107 | 1.772 ± 0.108 |
| LIVER | 1.349 ± 0.047 | 0.892 ± 0.083 |
| LUNG | 0.816 ± 0.031 | 0.525 – 0.053 |
| MUSCLE | 0.083 ± 0.009 | 0.050 ± 0.009 |
| TUMOR | — | 1.028 ± 0.158 |

[A](% Dose/Gram of Tissue)
[B]N = 3, Mean ± standard error
[C]Walker 256 Sarcoma implanted in Thigh

TABLE 4

DISTRIBUTION OF RADIOACTIVITY 24 HOURS AFTER IV ADMINISTRATION OF $^{125}I$-LABELLED ET-12IP-H IN NORMAL AND TUMOR-BEARING RATS[A,B]

| TISSUE | CONTROL | TUMOR[C] |
|---|---|---|
| BLOOD | 0.047 ± 0.035 | 0.036 ± 0.004 |
| KIDNEY | 0.257 ± 0.010 | 0.235 ± 0.018 |
| LIVER | 0.142 ± 0.033 | 0.139 ± 0.010 |
| LUNG | 0.129 ± 0.013 | 0.105 – 0.008 |
| MUSCLE | 0.025 ± 0.001 | 0.014 ± 0.001 |
| TUMOR | — | 0.463 ± 0.063 |

[A](% Dose/Grain of Tissue)
[B]N = 3, Mean ± standard error
[C]Walker 256 Sarcoma implanted in Thigh Six hours following the administration of ET-12IP-OMe, the radioactivity was distributed throughout the tissues studied with liver, kidney, and tumor tissues exhibiting the highest concentrations. However, by 24 hours, radioactivity had cleared significantly from all of the tissues except for tumor tissue.

Additional tissue distribution studies were conducted with the alkyl lysophospholipid analogues of general Formula I. The results are set forth in Table 5 hereinbelow. The distribution of radioactivity in various tissues was measured 24 hours after I.V. administration of the identified radioiodinated phospholipid ether analogues to Sprague-Dawley rats bearing the Walker-256 carcinosarcoma.

TABLE 5

| | Alkyl Phospholipid Ether Analogues* | | | |
|---|---|---|---|---|
| Tissue | Y = OCH$_3$ | Y = H | Y = OC(CH$_2$)$_{13}$CH$_3$ | Y = OH |
| Adrenal | 0.436 + 0.055 | 0.274 + 0.012 | 0.995 | 0.412 |
| Blood | 0.096 + 0.023 | 0.036 + 0.004 | 0.100 | 0.047 |
| Kidney | 0.463 + 0.111 | 0.235 + 0.018 | 0.259 | 0.510 |
| Liver | 0.743 + 0.105 | 0.139 + 0.010 | 0.489 | 0.234 |
| Lung | 0.299 + 0.017 | 0.105 + 0.008 | 0.235 | 0.525 |
| Muscle | 0.027 + 0.006 | 0.014 + 0.001 | 0.059 | 0.047 |
| Thyroid | 7.338 + 6.055 | 8.448 + 0.675 | 2.180 | 9.174 |
| Tumor | 1.115 + 0.016 | 0.463 + 0.063 | 0.456 | 0.570 |

*Formula I: where n = 12, Z = —N(CH$_3$)$_3$, and Y is given in Table 5

Scintigraphic Studies

Comparative studies using the compounds of the present invention and the prior art as scintigraphic agents were conducted. Radiolabelled ET-12IP-OMe and gallium-67 citrate were administered separately to rats bearing either tumors or inflammatory lesions. Both types of lesions were located in the thigh of the rat. Tumor bearing lesions were produced by implantation of Walker 256 sarcoma cells and inflammatory granuloma lesions were developed using carrageenan irritation in accordance with the method described by Atkinson, et al., *Agents and Actions*, Vol. 8, pages 263–267, 1978.

The distribution of ET-12IP-OMe and gallium-67 citrate were compared 24 hours after administration of the agents by whole body scans using gamma counter scintigraphy. Although gallium-67 citrate was found to localize in the inflammatory lesion, little activity was associated with this area following administration of the radiolabelled phospholipid ether analogue. Therefore, external visualization of the inflammatory lesion was difficult using ET-12IP-OMe. However, both labelled agents were capable of localizing in the tumor, and therefore visualization of the tumor was possible.

Figure 4:
FIG. 4 is a depiction resulting from a gamma-camera scintigraphy scan of an entire tumor-bearing rat following administration of radioactive 1-[12-(m-iodophenyl)-dodecyl]-2-methyl-rac-glycero-3-phosphocholine.

FIG. 4 is a depiction resulting from a scintigraphic scan of an tumor-bearing entire rat. As illustrated, the dark mass designated as L corresponds to liver tissue, and the dark mass designated T corresponds to tumor tissue. This figure shows high accumulation of ET-12IP-OMe in tumor T, with lower accumulation in liver L.

Figure 5:
FIG. 5 is a depiction of a gamma-camera scintigraphy scan of the lower abdominal region of the rat of FIG. 4.

FIG. 5 is a depiction of a scintigraphic scan of the lower abdominal region of the tumor-bearing rat. This figure shows high accumulation of ET-12IP-OMe in tumor T, with lower accumulation in liver L.

Figure 6:
FIG. 6 is a depiction resulting from a gamma-camera scintigraphy scan of an entire rat bearing an inflammatory lesion (granuloma) following administration of radioactive 1-[12-(m-iodophenyl)-dodecyl]-2-methyl-rac-glycero-3-phosphocholine.

FIG. 6 is a depiction resulting from a scintigraphic scan of an entire granuloma-bearing rat. This figure shows low accumulation of ET-12IP-OMe in granuloma G (inflammatory lesion) in relation to liver L.

Figure 7:
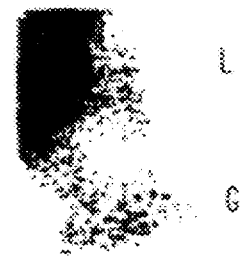
FIG. 7 is a depiction of a gamma-camera scintigraphy scan of the lower abdominal region of the rat of FIG. 6.

FIG. 7 is a depiction of a scan of the lower abdominal region of the granuloma-bearing rat. This figure shows low accumulation of ET-12IP-OMe in granuloma G (inflammatory lesion) in relation to liver L.

Figure 8:
FIG. 8 is a depiction resulting from a gamma-camera scintigraphy scan of an entire rat bearing an inflammatory lesion following administration of the prior art radiopharmaceutical, gallium-67 citrate.

FIG. 8 is a depiction resulting from a gamma-camera scintigraphic scan of an entire granuloma-bearing rat following administration of gallium-67 citrate. This figure shows high accumulation of $^{67}$Ga in granuloma G, as well as liver L.

Figure 9:
FIG. 9 is a depiction of a gamma-camera scintigraphy scan of the lower abdominal region of the rat of FIG. 8.

FIG. 9 is a depiction of a scan of the lower abdominal region of the granuloma-bearing rat following administration of gallium-67 citrate. This figure shows high accumulation of $^{67}$Ga in granuloma G, as well as liver L.

Figure 10:
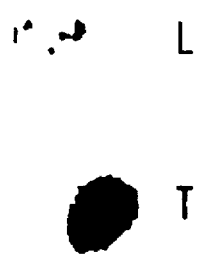
FIG. 10 is a depiction resulting from a gamma-camera scintigraphy scan of an entire rat bearing a tumor following administration of gallium-67 citrate.

FIG. 10 is a depiction resulting from a gamma-camera scintigraphy scan of an entire tumor-bearing rat following administration of gallium-67 citrate. This figure shows high accumulation of $^{67}$Ga in tumor T, and low accumulation in liver L.

Figure 11:
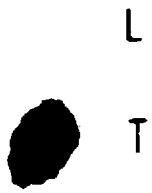
FIG. 11 is a depiction of a scan of the lower abdominal region of the rat of FIG. 10.

FIG. 11 is a depiction of a scan of the lower abdominal region of the tumor-bearing rat. This figure shows high accumulation of $^{67}$Ga in tumor T, and low accumulation in liver L.

Example 4:

This example illustrates another embodiment of the phospholipid ether analogues of the present invention wherein the monoiodinated benzoyl side chain is located at the 2-position on the triglycerol backbone in accordance with the general Formula II:

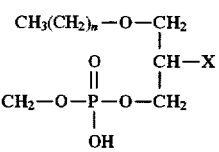

where n=1–15

Figure 12:
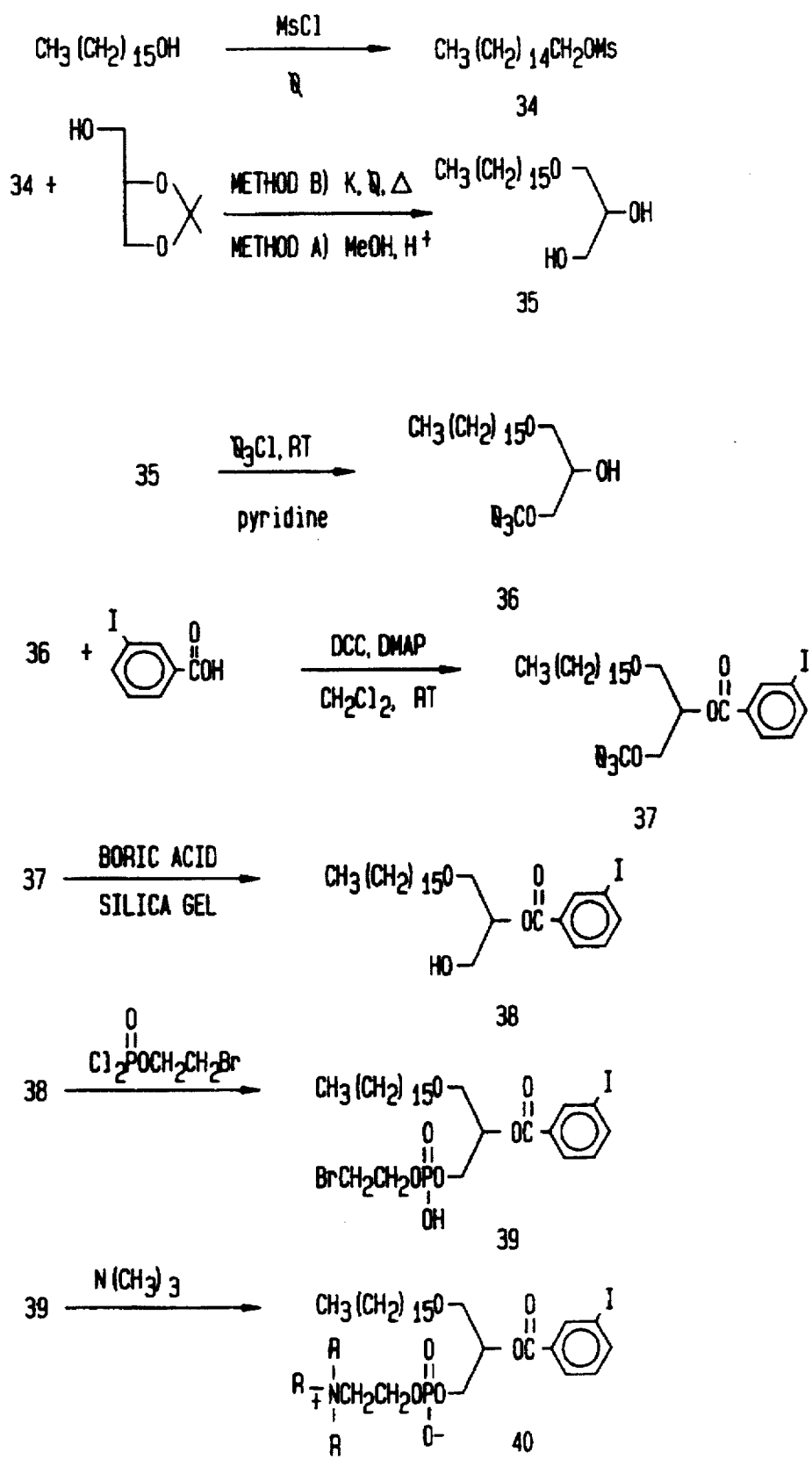
FIG. 12 is an illustrative preparatory scheme for rac-1-O-hexadecyl-2-O-iodobenzoyl-3-O-glycerolphosphocholine.
Figure 13:
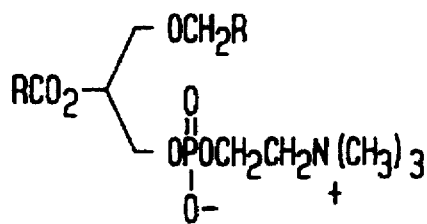
FIG. 13 shows the phospholipid ether catabolic pathway.
Figure 13:
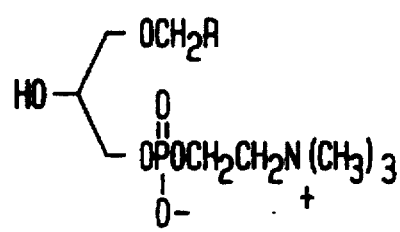
Figure 13:
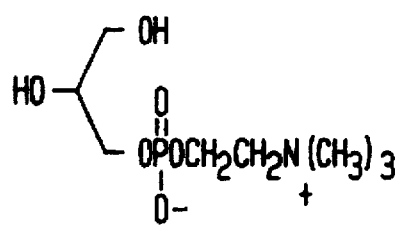

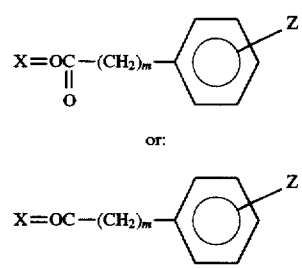

or:

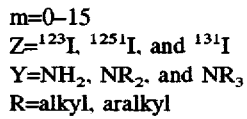

m=0–15
Z=$^{123}$I, $^{125}$I, and $^{131}$I
Y=NH$_2$, NR$_2$, and NR$_3$
R=alkyl, aralkyl FIG. 12 is an illustrative preparatory scheme for rac-1-O-hexadecyl-2-O-(m-iodobenzoyl)-3-O-glycerolphosphocholine.

Hexadecanol (6.94 g, 28.6 mmol) was placed into a flame-dried two-neck round-bottomed flask equipped with a reflux condenser and N$_2$ atmosphere. Anhydrous pyridine (40 ml) was added to the flask. The mixture was cooled to 0° C. before methane sulfonyl chloride (MsCl) was added. The solvent was removed to yield an oily residue. The crude product, or hexadecyl methansulfonate (compound 34) which contained a small amount of xylene, was used without further purification in the next step.

Method A

The crude material was transferred to a 100 ml round-bottomed flask equipped with a reflux condenser. Methanol (50 ml) and conc. HCl were added and the reaction mixture was refluxed several hours. After the reaction mixture had cooled to room temperature, the solvent-was removed and H2O and ether were added. The ether layer was extracted with H$_2$O, 1% NaHCO$_3$, and H$_2$O; dried with MgSO$_4$; and the solvent removed to provide a solid. Compound 35 was purified by recrystallization from petroleum ether to yield a white solid: rac-1-O-hexadecylglycerol (1.69 g, 55% based on the mesylate 34).

Method B

Potassium metal (1.5 g, 38.36 mmol) and anhydrous benzene (180 ml) were placed in a 500 ml three-neck round-bottomed flask equipped with a reflux condenser, dropping funnel, stir bar, and N$_2$ atmosphere. The reaction mixture was refluxed. When the potassium metal had melted, isopropylidene glycerol (6 ml, 48.25 mmol) was added dropwise and the reaction continued to reflux an additional 2.5 hours. A solution of hexadecyl methane sulfonate (10.0 g, 32.25 mmol) in anhydrous benzene (80 ml) was added dropwise and the reaction refluxed overnight. The heat was removed and the reaction mixture was coled to 0° C. Water was added and the benzene layer was removed, washed with H$_2$O, dried (MgSO$_4$) and filtered. This residue was treated as in METHOD A for the hydrolysis of the acetal group to provide compound 35, rac-1-O-hexadecylglycerol (7.65 g, 75%, based on mesylate 34).

rac-1-O-Hexadecylglycerol (1.3 g, 4.17 mmol) and anhydrous pyridine (20 ml) were placed in a flame-dried 50 ml round-bottomed flask flushed with N$_2$. Triphenylchloromethane (2.38 g, 8.54 mmol) was added to the solution and the reaction mixture was stirred for 48 hours. Ice cold H$_2$O and ether were added. The ethe r layer was removed, washed with H$_2$O, dried (MgSO$_4$), and filtered. The solvent was removed under reduced pressure. Residual pyridine was removed as an azeotrope with toluene. The resulting white solid was dissolved in petroleum ether, and the solution refluxed for one hour to precipitate the triphenyl-Oethanol. The solution was filtered and the petroleum ether removed to yield the crude product 36, rac-1-O-hexadecyl-3-O-tritylglycerol (2.73 g, theoretical yield =2.29 g ). The product was not purified further, but used directly in the next synthesis.

In a flame-dried round-bottomed flask flushed with N$_2$, crude rac-1-O-hexadecyl-3-O-tritylglycerol (400 mg) was dissolved in anhydrous CH$_2$Cl$_2$ (7 ml). m-Iodobenzoic acid (178 mg, 0.717 mmol) was added along with an additional amount of CH$_2$Cl$_2$ (3 ml). After the acid had dissolved, DCC (163 mg, 0.79 mmol) and DMAP (24 mg, 0.20 mmol) were added. The reaction mixture was stirred overnight at room temperature and then filtered. The filtrate was washed with H$_2$O, dried (MgSO$_4$), and the solvent removed to yield an oily residue. Compound 37, rac-1-O-hexadecyl-2-O-m-iodobenzoyl-3-O-tritylglycerol, was purified by column chromatography.

rac-1-O-Hexadecyl-2-O-m-iodobenzoyl-3-O-tritylglycerol (1.02 g, 1.29 mmol) was dissolved in petroleum ether (bp 30°-36° C.) and applied to a silica gel-boric acid column (13.46 g). The column was prepared following a known procedure. The elution of the column with petroleum ether (150 ml), petroleum ether:ether (95:5, 850 ml) and hexanes:ether (3:1, 400 ml) resulted in the removal of the trityl group and the isolation of the deprotected alcohol 38. The fractions containing compound 38 were combined and the solvent removed in vacuo. The residue was dissolved in CHCl$_3$, extracted with H$_2$O, and dried (MgSO$_4$). After the mixture was filtered, the solvent was evaporated to yield the pure compound 38, rac-1-O-hexadecyl-2-O-m-iodobenzoylglycerol.

Bromoethyl dichlorophosphate (100 mg, 0.416 mmol) and anhydrous ether were placed in a flame-dried three-neck 25 ml round-bottomed flask equipped with a reflux condenser and flushed with N$_2$. The solution was cooled to 0° C. before anhydrous pyridine (0.13 ml, 1.60 mmol) followed by a solution of rac-1-O-hexadecyl-2-O-m-iodobenzoylglycerol (62.9 mg, 0.115 mmol) in anhydrous ether (4 ml) were added. The reaction mixture was stirred at 0° C. for 10 minutes and was then heated at reflux for 3.5 hours. The reaction mixture was allowed to cool to room temperature before the solvent was removed. A mixture of CHCl$_3$ and H$_2$O were added. The CHCl$_3$ layer was removed and washed with H$_2$O and the solvent was evaporated under pressure. The residue was purified by column chromatography (10 g silica gel, CHCl$_3$:CH$_3$OH, 9:1) to yield the pure compound 39: rac-1-O-hexadecyl-2-O-m-iodobenzoyl-3-O-(2'-bromoethyl)-phosphoryl glycerol (56 mg, 36.4%).

rac-1-O-Hexadecyl-2-O-m-iodobenzoyl-3-O-(2'-bromoethyl)-phosphoryl glycerol (42.0 mg, 57.3 mmol) was placed into a two-neck 25 ml round-bottomed flask equipped with a reflux condenser. A mixture of CHCl$_3$:isopropanol:DMF (6 ml, 3:5:5) was added which was followed by the addition of an aqueous solution of N(CH$_3$)$_3$ (0.42 ml, 2.86 mmol, 7.1 M). The reaction mixture was heated to 60° C. and maintained for 4 hours. The heat was removed and the reaction was allowed to cool to room temperature before AgCO$_3$ (35 mg, 0.12 mmol) was added. The reaction mixture was heated for another hour and then allowed to cool to room temperature before being filtered. The solvent was removed and the residue dissolved in CHCl$_3$. The CHCl$_3$ solution was washed with H$_2$O. Methanol was used to break up the emulsions which formed. The solvent was removed under reduced pressure and the residue was purified by column chromatography (10 g silica gel, CHCl$_3$:CHCl$_3$OH:H$_2$O) to provide the phospholipid 40: rac-1-O-hexadecyl-2-O-m-iodobenzoyl-3-O-glycerophosphocholine (15 mg, 36.8%).

Tissue distribution studies were conducted with the alkyl lysophospholipid analogues of general Formula II. The results are set forth in Table 6 hereinbelow. The distribution of radioactivity in various tissues was measured 24 hours after I.V. administration of the identified radioiodinated phospholipid ether analogues to Sprague-Dawley rats bearing the Walker-256 carcinosarcoma.

TABLE 6

| | Alkyl Phospholipid Ether Analogues* | | |
|---|---|---|---|
| Tissue | X = COOIB#, R = CH$_3$ | X = OIB, R = CH$_3$ | X = OCH$_3$, R = CH$_2$IB |
| Adrenal | 0.463 + 0.045 | 0.552 + 0.091 | 0.320 |
| Blood | 0.107 + 0.007 | 0.071 + 0.010 | 0.013 |
| Kidney | 0.560 + 0.078 | 0.351 + 0.045 | 0.156 |
| Liver | 1.530 + 0.067 | 1.395 + 0.187 | 0.228 |
| Lung | 1.030 + 0.145 | 0.496 + 0.068 | 0.325 |
| Muscle | 0.038 + 0.002 | 0.029 + 0.005 | 0.025 |
| Thyroid | 55.680 + 5.378 | 1.370 + 0.153 | 2.044 |
| Tumor | 0.729 + 0.085 | 0.239 + 0.005 | 0.378 |

*Formula II: where n = 15, Y = N(CH$_3$)$_2$R, and X and R are given in Table 6
IB = iodobenzyl Example 5:

It should be noted that when the 2-position substituent of the triglycerol backbone structure of the general Formula I is acetyl, the phospholipid ether analogues of the present invention would be analogues of platelet activating factor, and thus, would become useful as tracers for metabolic studies dealing with platelet activating factor.

Alkyl Phosphocholine Analogues

Phospholipids are esters of phosphoric acid which contain one or two molecules of fatty acid, an alcohol and a nitrogenous base. The foregoing examples were directed to radioiodinated analogues of the naturally-occurring phospholipid ether, alkyl lysophospholipid. However, an integral part of the structure of the alkyl lysophospholipid analogues of the type described hereinabove is the phosphocholine moiety:

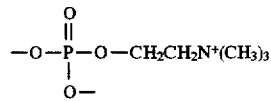

Alkyl Phosphocholine

The phospholipid ether analogues heretofore described have a triglycerol backbone structure which is substituted at the 3-position with an alkyl phosphocholine and include a monoiodinated benzoyl side chain substituted at either the 1- or 2-position. In additional embodiments of the invention, such as those illustrated in Examples 6 and 7, a monoiodinated aralkyl side chain may be substituted directly onto the alkyl phosphocholine moiety in accordance with general Formula III:

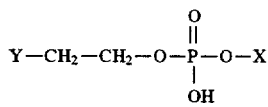

where
Y=$NH_2$, $NR_2$, $NR_3$, $NR_2R'$
R=alkyl, aralkyl
R'=a monoiodinated aralkyl, such as

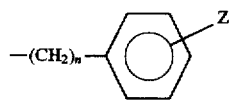

Z=$^{122}I$, $^{123}I$, $^{125}I$, and $^{131}I$
n=1-15

X=a monoiodinated aralkyl, like R', where n=1-15; or an alkyl, such as —$CH_2$—$(CH)_m$—$CH_3$, where m=1-15
Provided, however, that one, and only one, of X or Y is a monoiodinated aralkyl.

The resulting alkyl phosphocholine analogues are less complex and have been found to give extraordinary results when used as radiopharmaceuticals. Moreover, the alkylphosphocholine compounds have been found to localize in tumors and neoplastic lesion. This characteristic is advantageous both for imaging and therapeutic purposes since less damage is propagated to surrounding tissue. Moreover, in those embodiments of the invention wherein the alkyl phosphocholine analogue is radiolabeled with long-lived $^{131}I$, for example, for therapeutic purposes, the destructive radiation is more evenly distributed within the cancerous tissue.

Two specific illustrative embodiments of radioiodinated alkyl phosphocholine analogues of the present invention are derived from the alkyl phosphocholine, hexadecyl phosphocholine: 12-(m-iodophenyl)-dodecyl phosphocholine (Example 6) and hexadecyl-2-[N,N-dimethyl-N-(m-iodobenzyl)-ammonium] ethylphosphate (Example 7).

Figure 14:
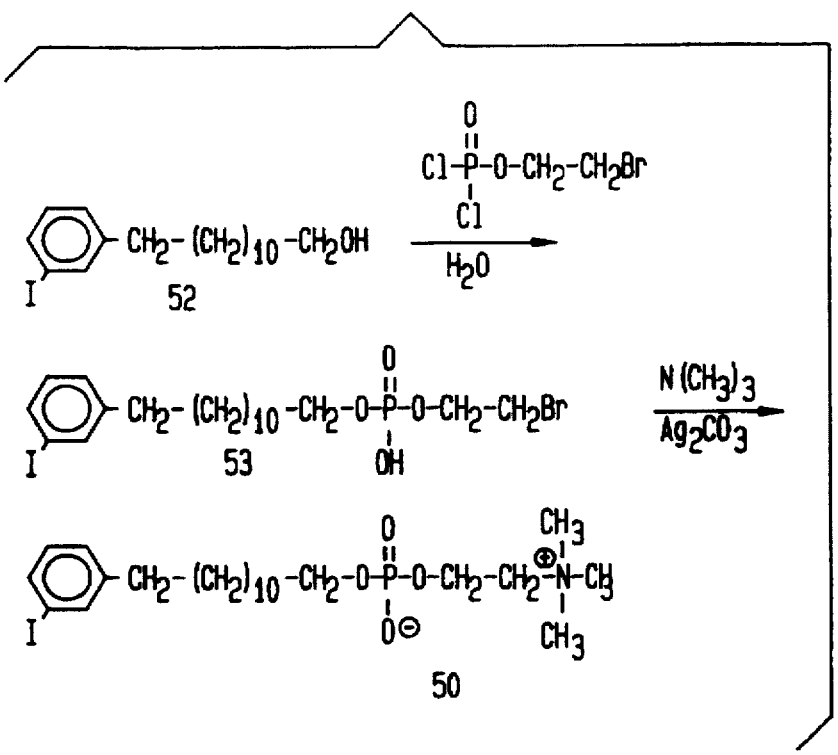
FIG. 14 is an illustrative preparatory scheme for 12-(m-iodophenyl)-dodecyl phosphocholine.
Figure 15:
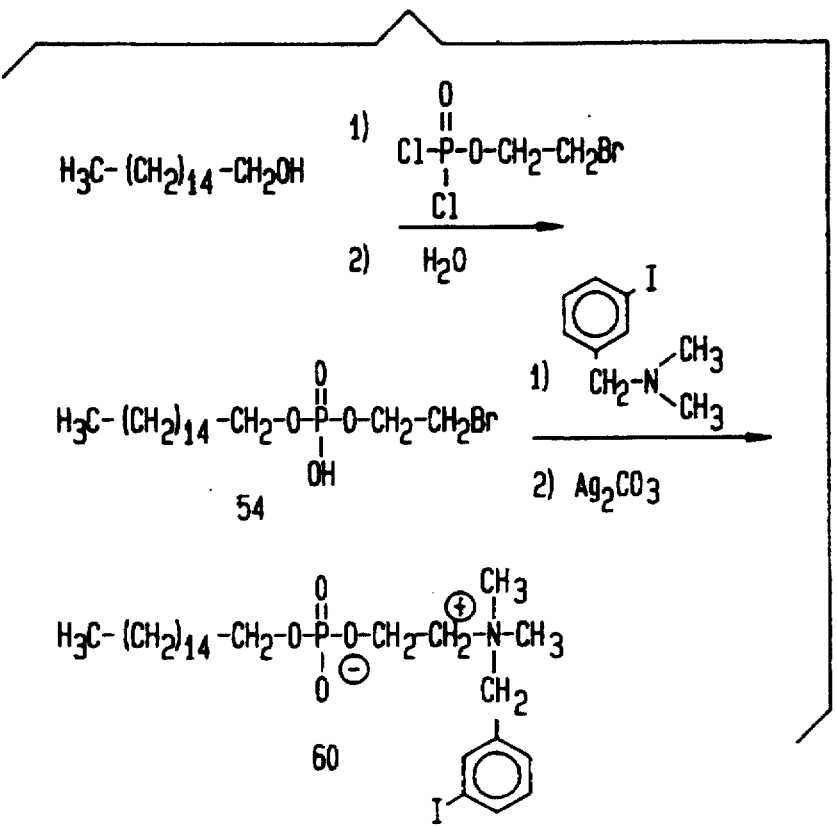
FIG. 15 is an illustrative preparatory scheme for hexadecyl-2-[N,N,-dimethyl-N-(m-iodobenzyl)-ammonium] ethylphosphate.

12-(m-Iodophenyl)-dodecyl phosphocholine (compound 50) and hexadecyl-2-[N,N-dimethyl-N-(m-iodobenzyl)-ammonium] ethylphosphate (compound 60) were synthesized in accordance with the illustrative preparatory scheme shown in FIGS. 14 and 15. Phosphorylation of 12-(m-iodophenyl)dodecanol (compound 52) and hexadecanol with 2-bromoethyl dichlorophosphate resulted in the production of 12-(m-iodophenyl)-dodecyl-2-bromoethylphosphate (compound 53; 63% yield) and hexadecyl-2-bromoethylphosphate (compound 54; 43% yield). Phosphate compound 53 was readily converted to the choline phosphate compound 50 by heating it with trimethyl amine in $CHCl_3$:isopropyl alcohol:DMF (3:5:5) for 6 hours (yield 62%). Condensation of phosphate compound 54 and m-iodobenzylamine (compound 55) was carried out by refluxing these reagents in ethanol for 3 days. The resulting product was the N-iodobenzyl derivative compound 60 (yield 29%).

Example 6:

In a specific illustrative embodiment of the invention, the synthesis of 12-(m-iodophenyl)dodecyl phosphocholine (compound 50) was accomplished in accordance with the illustrative preparatory scheme of FIG. 14.

A solution of (m-iodophenyl)dodecanol (compound 52) (110 mg, 0.28 mmol) in dry ether (2 ml) and $N(CH_2CH_3)_3$ (0.05 ml, 0.36 mmol) was cooled over ice. A solution of 2-bromoethyl dichlorophosphate (83 mg, 0.34 mmol) in dry ether (1.5 ml) was added dropwise to the solution of compound 52. The resulting mixture was stirred at 0° C. for 10 minutes and then gently refluxed for 3 hours. Additional dichlorophosphate (68 mg) and $N(CH_2CH_3)_3$ (0.04 ml) were added to the mixture and refluxing was continued for another 3 hours. Water (1 ml) was then added to the mixture and refluxing was continued for yet another 2 hours. The solvent was stripped from the mixture and the residue was dissolved in $CHCl_3$. The dissolved residue was washed successively with $H_2O$, 0.1 N HCl, and $H_2O$, and then dried over $MgSO_4$. The $CHCl_3$ was evaporated to leave a dry residue. The residue was purified on a silica gel chromatography column eluted with $CHCl_3$:$CH_3OH$ (15:1) to remove less polar impurities, and then with $CHCl_3$:methanol (8:1) to remove the pure intermediate compound 53 (101 mg, 62%). The pure intermediate was a glassy solid which was utilized in the next step of the synthesis without further processing.

A mixture of compound 53 (101 mg, 0.18 mmol) and $N(CH_3)_3$ (1.3 ml, 45–50% aq. solution) was dissolved in $CHCL_3$:DMF:isopropanol (3:5:5, 10 ml) and stirred for 6 hours at 60° C. The mixture was then cooled prior to adding $Ag_2CO_3$ (63 mg). Heating was resumed for 2 additional hours. The silver salts were removed by filtration through Celite and the filtrate was concentrated to dryness. The dry residue was purified on a silica gel chromatography column. Elution with $CHCl_3$:methanol (3:1) removed starting material (Compound 53, 23 mg). Subsequent elution with $CHCl_3$:methanol:$H_2O$ (65:25:3) removed pure compound 50 as a white solid (59 mg, yield 61%).

Example 7:

In a further specific embodiment of the invention, hexadecyl-2-[N,N-dimethyl-N-(m-iodobenzyl)-ammonium] ethylphosphate (Compound 60) was prepared in accordance with the illustrative preparatory scheme of FIG. 15.

A solution of hexadecanol (500 mg, 2.06 mmol) in dry ether (15 ml) and $N(CH_2CH_3)_3$ (0.36 ml, 2.60 mmol) was cooled over ice. A solution of 2-bromoethyl dichlorophosphate (600 mg, 2.48 mmol) in dry ether (10 ml) was added dropwise to the solution of hexadecanol. The resulting mixture was stirred at 0° C. for 10 minutes and then gently refluxed for 4.5 hours. The mixture was cooled. Water (3.5 ml) was added to the cooled mixture and refluxing was continued for another 2 hours at 60° C. The solvent was stripped from the mixture and the resulting residue was dissolved in $CHCl_3$. The dissolved residue was washed successively with $H_2O$, 0.1 N HCl, and $H_2O$, and then dried over $MgSO_4$. The $CHCl_3$ was evaporated to leave a dry residue. The residue was purified on a silica gel chromatography column eluted with $CHCl_3$:methanol (15:1) and then with $CHCl_3$:methanol (8:1) to yield the pure intermediate compound 54 (376 mg, 43%). The pure intermediate was a white solid which was utilized in the next step of the synthesis without further processing.

A mixture of compound 54 (100 mg, 0.23 mmol) and N,N-dimethyl-m-iodobenzyl-amine (304 mg, 1.16 mmol) was dissolved in ethanol (5 ml) and refluxed for 3 days.

Ag$_2$CO$_3$ (83 mg) was added and refluxing was continued for an additional 2 hours. The silver salts were removed by filtration, and the filtrate was concentrated to dryness under reduced pressure. The residue was purified by chromatography on silica gel with CHCl$_3$:methanol (3:1) to produce pure compound 60 (41.5 mg, 29%) as a white solid.

Of course, the alkyl phosphocholine analogues of the type illustrated in Examples 6 and 7 can be radiolabelled, such as by any of the techniques described hereinabove.

Example 8:
In Vivo Testing of the Compounds of Examples 6 and 7

Figure 16:
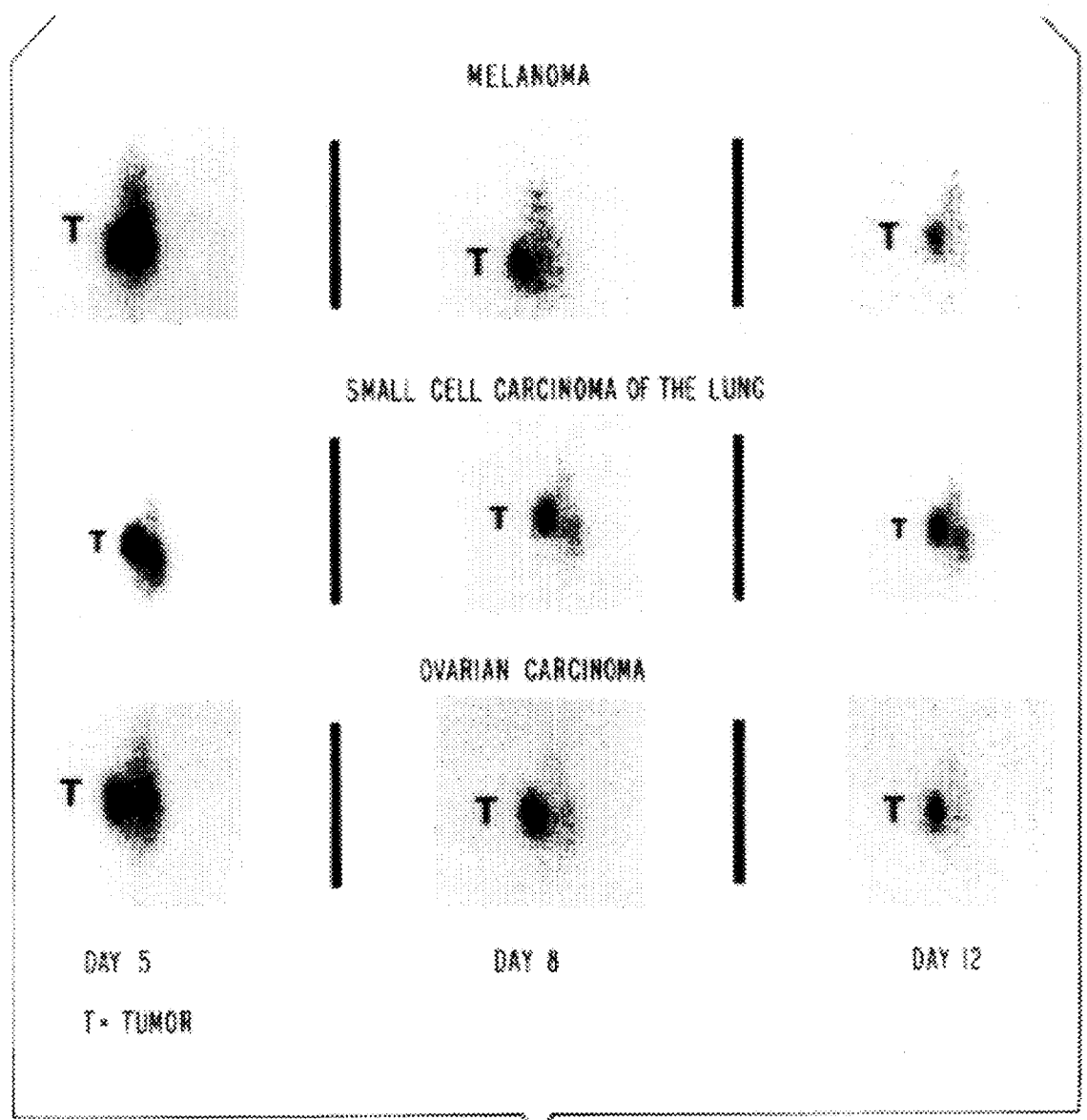
FIG. 16 shows whole body gamma-camera scintigraphy scans of athymic nude mice bearing the human tumors (1) small cell carcinoma, (2) malignant melanoma, and (3) ovarian adenocarcinoma taken at 5 days, 8 days, and 12 days post-administration of radioiodinated 12-(m-iodophenyl)-dodecyl phosphocholine.

12-(m-Iodophenyl)dodecyl phosphocholine (compound 50) was administered by intravenous injection to Sprague-Dawley rats with intramuscular Walker 256 sarcomas and athymic nude mice with subcutaneous human tumors, specifically, human HTB 77 ovarian adenocarcinoma, NCI 69 human small cell carcinoma, and human HTB 63 melanoma. Administration of compound 50 resulted in excellent tumor localization in all models tested. FIG. 16 shows whole body gamma-camera scintigraphy scans of athymic nude mice bearing the human tumors referred to hereinabove which were taken at intervals over an extended period of time. More specifically, FIG. 16 shows scans taken at 5 days, 8 days, and 12 days post-administration. Tumor imaging was particularly striking after beyond five days post-injection when all background activity had cleared from the liver and gastrointestinal tract.

Similar studies were conducted with hexadecyl-2-[N,N,-dimethyl-N-(m-iodobenzyl) ammonium] ethylphosphate (compound 60). Compound 60 also exhibited localization in tumor tissues.

Figure 17:
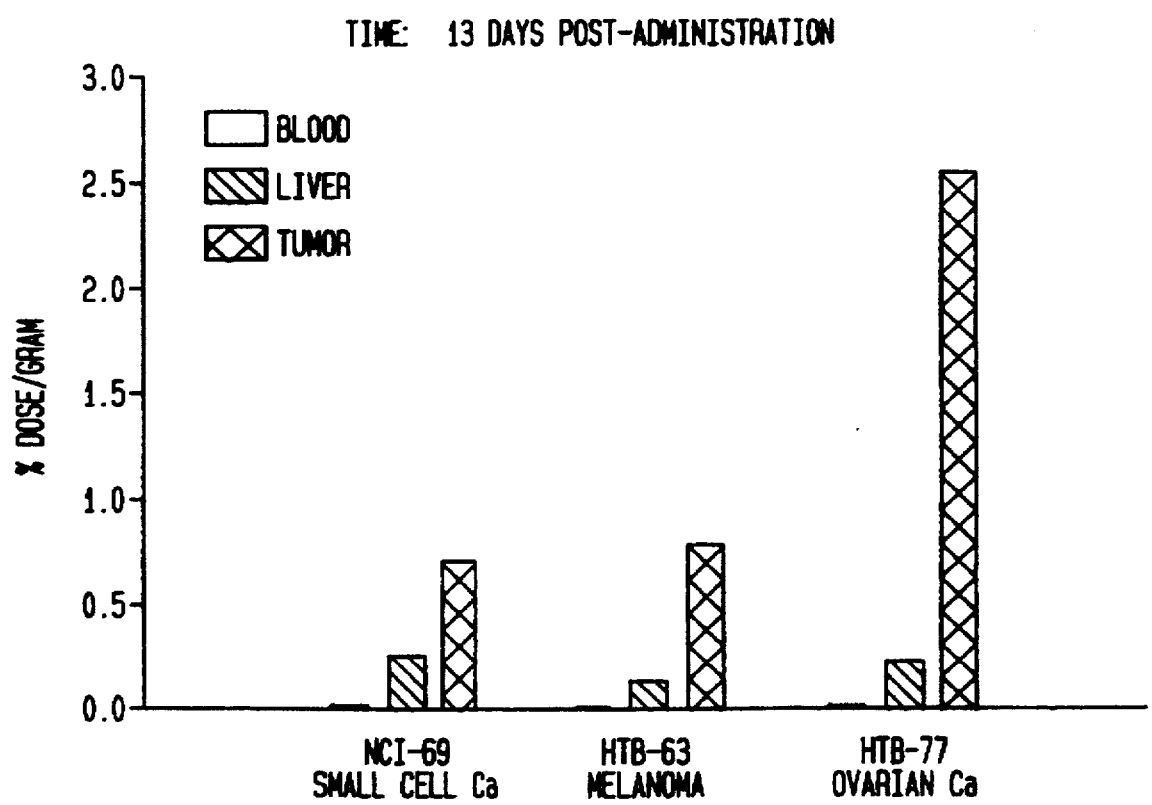
FIG. 17 is a bar graph showing tissue distribution in the blood, liver, and specified tumor tissue of radioiodinated 12-(m-iodophenyl)-dodecyl phosphocholine in nude mice 13 days post-administration.

The results of tissue distribution studies, as shown in FIGS. 17 and 18, were consistent with the scintigraphic scans of FIG. 16. Tumor:blood levels greater than 25:1 were recorded in all athymic mice human tumor models.

FIG. 17 is a bar graph showing the tissue distribution in the blood, liver, and specified tumor tissue of compound 50 in nude mice 13 days post-administration. The data is expressed in terms of % dose/gram of tissue. In each case, the tumor contained the largest amount of radioactivity.

FIG. 18 is a bar graph which vividly illustrates the relative difference in tissue concentration of compound 50 in nude mice bearing HTB 63 human melanoma tumors at 13 days post-injection. The tissue concentration in the tumor tissue is remarkable.

Advantageously, the truncated phospholipid ether analogues of the present invention, in particular, tend to accumulate in the center, or necrotic region, of the tumor as evidenced by autoradiography studies of cross-sectional slices of athymic nude mice tumors. Thus, usage of these compounds as imaging agents and/or therapeutic agents is safer than usage of prior art imaging agents because less damage is propagated to surrounding tissue. Furthermore, the accumulation in the center of the tumor results in better distribution of destructive radiation within the tumor for therapeutic applications.

In addition to the foregoing, the alkyl phosphocholine analogues of the present invention are membrane specific inasmuch as they approximate the normal constituents of cell membranes. Cellular uptake studies on compound 50, for example, have confirmed the specificity for the cellular membranes. It is postulated that membrane debris remains after the rapidly dividing cancer cells die, and therefore, the membrane-bound compounds of the present invention localize and remain in place for diagnostic and/or therapeutic applications.

As yet an additional advantage, it should be noted that all of the phospholipid ether analogues of the present invention are cytotoxic, even without the presence of a radioactive isotope in the molecule. Therefore, the inclusion of a long-lived radioactive isotope of iodine, for example, yields radiopharmaceuticals which are tissue-destructive by more than one mode.

In addition to the foregoing specifically mentioned uses of the inventive compounds, the compounds of the present invention may find applicability as carrier molecules for radiosensitizers. Radiosensitizers are agents administered to sensitize tumor tissue to the effects of externally applied radiation. Well known radiosensitizers, such as misonidazole and metronidazole are substituted nitroimidazoles. Substitution of an electron-capturing moiety, such as nitroimidazole, for the iodophenyl moiety in the phospholipid ether analogues of the present invention would permit tumor-localized sensitization for radiation therapy.

In yet another proposed use, the phospholipid analogues of the present invention could incorporate boron-containing substituents for use as boron-neutron activation therapeutic agents. These therapeutic agents are administered using the stable isotope of the electron-capturing boron. External radiation activates the boron to create tissue destructive activity.

Although the invention has been described in terms of specific embodiments and applications, persons skilled in this art can, in light of this teaching, generate additional embodiments without exceeding the scope or departing from the spirit of the claimed invention. In particular, the methods of synthesis are merely illustrative and can be modified by those of skill in the art for the production of various substituted phospholipid ether analogues in accordance with the invention. Moreover, other techniques of radio-tagging the analogues may be employed. Of course, the invention contemplates any one of the ortho-, meta- and paraisomers of iodobenzyl as the iodine-bearing moiety. Accordingly, it is to be understood that the drawings and descriptions in this disclosure are proffered to facilitate the comprehension of the invention and should not be construed to limit the scope thereof.

Wath is claimed is:

1. A compound having the general formula:

$$\begin{array}{c} CH_3(CH_2)_n-O-CH_2 \\ | \\ O \quad\quad CH-X \\ \| \quad\quad | \\ Y-CH_2-CH_2-O-P-O-CH_2 \\ | \\ OH \end{array}$$

where n=1–15, except n=1–14 where m=0 and Y=—N(CH$_3$)$_3$; X is selected from the group consisting of

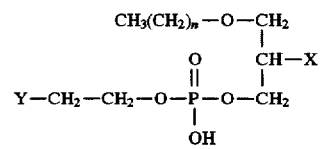

and

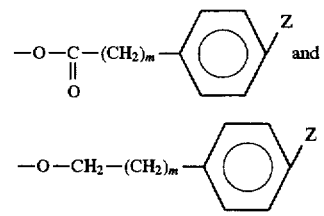

where m=0–15 and Z is a radioactive isotope of iodine; Y is selected from the group consisting of NH$_2$, NR$_2$, NR$_3$; and R is selected from the group consisting of alkyl and aralkyl substituents.

2. The compound of claim 1 wherein Z is selected from the group consisting of $^{122}$I, $^{123}$I, $^{125}$I, and $^{131}$I.

* * * * *